(12) United States Patent
Krishnan et al.

(10) Patent No.: US 11,806,155 B2
(45) Date of Patent: Nov. 7, 2023

(54) SYSTEM AND METHOD FOR QRS COMPLEX DETECTION IN COMPRESSIVELY SENSED ELECTROCARDIOGRAM DATA

(71) Applicants: Sridhar (sri) Krishnan, Richmond Hill (CA); Jeevan Kumar Pant, Toronto (CA)

(72) Inventors: Sridhar (sri) Krishnan, Richmond Hill (CA); Jeevan Kumar Pant, Toronto (CA)

(*) Notice: Subject to any disclaimer, the term of this patent is extended or adjusted under 35 U.S.C. 154(b) by 572 days.

(21) Appl. No.: 16/612,266

(22) PCT Filed: May 11, 2017

(86) PCT No.: PCT/CA2017/050567
§ 371 (c)(1),
(2) Date: Nov. 8, 2019

(87) PCT Pub. No.: WO2018/205007
PCT Pub. Date: Nov. 15, 2018

(65) Prior Publication Data
US 2020/0060570 A1 Feb. 27, 2020

(51) Int. Cl.
*A61B 5/36* (2021.01)
*A61B 5/366* (2021.01)
*A61B 5/00* (2006.01)
*H03M 7/30* (2006.01)

(52) U.S. Cl.
CPC ............ *A61B 5/366* (2021.01); *A61B 5/0006* (2013.01); *A61B 5/7225* (2013.01); *A61B 5/7232* (2013.01); *H03M 7/3062* (2013.01)

(58) Field of Classification Search
CPC ...... A61B 5/7232; A61B 5/0006; A61B 5/349
See application file for complete search history.

(56) References Cited

U.S. PATENT DOCUMENTS

2011/0077538 A1* 3/2011 Liu .................. A61B 5/726
600/509

OTHER PUBLICATIONS

Pan, Jaipu and Tompkins, Willis J. 1985. "A real-time QRS detection algorithm". IEEE Transactions on Biomedical Engineering. vol. BME-32, Issue: 3, Mar. 1985. pp. 230-236.

(Continued)

*Primary Examiner* — Michael J D'Abreu

(57) ABSTRACT

Electrocardiogram (ECG) data is compressible at high compression ratios using suitable compressive sensing techniques. Methods of detecting QRS complexes in an ECG signal may comprise receiving compressively-sensed measurements of an ECG signal; constructing an estimate of the ECG signal from the received compressively-sensed measurements, and detecting QRS complexes in the estimate of the ECG signal. QRS complexes may be detected by computing the first-order difference of the estimate of the ECG signal and processing the first-order difference of the estimate of the ECG signal to locate one or more significant natural blocks, each indicating a QRS complex in the ECG signal. QRS complexes may also be detected by using a conventional QRS detection algorithm on the estimate of the ECG signal. Also disclosed are related systems for detecting QRS complexes and for compressively sensing ECG signals.

13 Claims, 20 Drawing Sheets

(56) References Cited

OTHER PUBLICATIONS

Pant, Jeevan and Krishnan, Sridhar. 2016. "Compressive sensing of foot-gait signals by enhancing group block-sparse structure on the first-order difference". Conference proceedings: . . . Annual International Conference of the IEEE Engineering in Medicine and Biology Society (EMBC). IEEE Engineering in Medicine and Biology Society. Conference. Aug. 2016. 3700-3703.

Pant, Jeevan and Krishnan, Sridhar. 2016. "Compressive Sensing of Foot Gait Signals and Its Application for the Estimation of Clinically Relevant Time Series". IEEE Transactions on Biomedical Engineering. vol. 63, Issue: 7, Jul. 2016. pp. 1401-1415.

Pant, Jeevan and Krishnan, Sridhar. 2016. "Efficient compressive sensing of ECG segments based on machine learning for QRS-based arrhythmia detection". Conference proceedings: . . . Annual International Conference of the IEEE Engineering in Medicine and Biology Society (EMBC). IEEE Engineering in Medicine and Biology Society. Conference. Aug. 2016. 4731-4734.

\* cited by examiner

SYSTEM AND METHOD FOR QRS COMPLEX DETECTION IN COMPRESSIVELY SENSED ELECTROCARDIOGRAM DATA

FIELD

This application is a national stage application pursuant to 35 U.S.C. § 371 of PCT/CA2017/050567, filed May 11, 2017. This relates to electrocardiograms and, more particularly, to the detection of QRS complexes in electrocardiogram data collected using compressive sensing techniques.

BACKGROUND

In electrocardiography (ECG or EKG) the electrical activity of the heart is monitored using, for example, electrodes that are placed on the skin of a patient. Traditionally, electrocardiograms are interpreted by skilled human operators such as, for example, physicians or cardiologists. ECG data may also be interpreted using computer algorithms.

Heart rhythms produce formations in electrocardiograms, common ones of which are known as entities. More particularly, normal heart rhythms produce four entities: a P wave, representing atrial depolarization, a QRS complex representing ventricular depolarization, a T wave representing ventricular repolarization, and a U wave, representing papillary muscle repolarization.

Automated detection of these QRS complexes or formations can thus allow for automated interpretation of ECGs. In some cases, detection of particular ones of these entities is important for analysis applications. For example, detection of the QRS complex may allow for detection of pathologies such as, for example, heart arrhythmias.

Applications such as mobile arrhythmia monitors for ambulatory patients require very accurate QRS segment recognition so that the ECG can be properly analyzed. False detection can have negative implications such as, for example, misreading or unnecessary collection or transmission of data. Misreading may result in unnecessary follow-up and potentially, therefore, in wasted physician resources.

Detection of QRS segments for electrocardiogram signals has remained an active research area for over forty years. The most well-known algorithm for QRS detection is one proposed by Pan and Tompkins: the "Pan-Tompkins algorithm". The Pan-Tompkins algorithm is described in "A Real-time QRS Detection Algorithm" by J. Pan and W. J. Tompkins published in IEEE Trans. Biomed. Eng. Vol. BME-32, No. 3, pages 230-236, March 1985, the entire contents of which are herein incorporated by reference.

A modified version of the Pan-Tompkins algorithm was presented by Hamilton and Tompkins in "Quantitative Investigation of QRS Detection Rules using the MIT/BIH Arrhythmia Database" IEEE Trans. Biomed. Eng., Vol. BME-33, No. 12, pages 1157-1165, December 1986, the entire contents of which are herein incorporated by reference (the "Hamilton-Tompkins algorithm").

Various other QRS detection algorithms have appeared in the literature, however, the Pan-Tompkins and Hamilton-Tompkins algorithms have been well favored for their simplicity and low computational cost.

Recently, compressive sensing or compressed sensing (CS) that uses low power sensing for the acquisition of physiological signals has drawn the attention of the bio-sensing research community. In compressed sensing, signals are compressed in a mathematically lossy fashion and then later reconstructed by finding solutions to underdetermined linear systems. By constraining the solutions to be sparse, that is, having only a small number of non-zero coefficients, signals having a sparse structure may be re-constructed using a number of samples less than may otherwise be suggested to be required according to the Shannon-Nyquist sampling theorem and more traditional signal processing techniques.

Existing QRS detection algorithms, including the Pan-Tompkins and the Hamilton-Tompkins algorithm, are not intended for use with compressively sensed ECG data. Instead, most are typically employed on uncompressed ECG data. Moreover, existing algorithms for ECG signal reconstruction perform poorly for compressive sensing with higher compression ratio, especially for compression ratios in excess of 71%. Further, existing methods for ECG signal reconstruction from compressively sensed data are not tailored for QRS detection.

SUMMARY

Herein disclosed are signal reconstruction algorithms tailored to physiological signals that, when used in concert with a technique for QRS segment detection also disclosed herein, allow QRS segments to be detected from compressively sensed ECG measurements.

In an aspect, there is provided a method of detecting QRS complexes in an ECG signal, the method comprising: receiving compressively-sensed measurements of the ECG signal; constructing an estimate of the ECG signal from the received compressively-sensed measurements; computing the first-order difference of the estimate of the ECG signal; and processing the first-order difference of the estimate of the ECG signal to locate one or more significant natural blocks, each indicating a QRS complex in the ECG signal.

In another aspect, there is provided system for detecting QRS complexes in ECG signals, the system comprising: a receiver for receiving compressively-sensed measurements of an ECG signal; a processor coupled to a non-transitory computer-readable storage medium, the medium storing instructions that when executed by the processor cause the processor to perform the foregoing method.

In another aspect, there is provided a system for detecting QRS complexes in ECG signals, the system comprising: a receiver for receiving compressively-sensed measurements of an ECG signal; a processor coupled to a non-transitory computer-readable storage medium, the medium storing instructions that when executed by the processor cause the processor to: construct an estimate of the ECG signal from the received compressively-sensed measurements; compute the first-order difference of the estimate of the ECG signal; and process the first-order difference of the estimate of the ECG signal to locate one or more significant natural blocks, each indicating a QRS complex in the ECG signal.

In another aspect, there is provided a method of detecting QRS complexes in an ECG signal, the method comprising: receiving compressively-sensed measurements of the ECG signal; constructing an estimate of the ECG signal from the received compressively-sensed measurements; and detecting QRS complexes in the ECG signal by applying a conventional QRS complex detection algorithm to the estimate of the ECG signal.

In another aspect, there is provided a system for detecting QRS complexes in ECG signals, the system comprising: a receiver for receiving a compressively-sensed measurements of an ECG signal; a processor coupled to a non-transitory computer-readable storage medium, the medium storing instructions that when executed by the processor cause the processor to perform the foregoing method.

Conveniently, in this way, QRS complexes may be detected from compressively sensed ECG data. Further, conveniently, high compressive ratios (>60%) may be employed without significant impairment of QRS detection effectiveness.

BRIEF DESCRIPTION OF THE DRAWINGS

Embodiments are described in detail below, with reference to the following drawings.

as shown in FIG. 22) may operate.

DETAILED DESCRIPTION

Compressive or compressed sensing (CS) is a technique developed for the acquisition of sparse signal from a small number of measurements. In compressive sensing, if a vector x of length N denotes signal segment, its measurement vector y of length M with M<<N can be obtained as y where:

$$y = \phi x \quad (1)$$

and where $\phi$ is a measurement matrix of size M×N. A measurement matrix $\phi$ can be selected using well-known techniques as known to skilled persons.

In some embodiments, a measurement matrix $\phi$ can be selected so as to limit the amount of computation required for multiplying it with the signal vector x. Additionally or alternatively, measurement matrix $\phi$ may be selected so as to limit storage space. For example, measurement matrix $\phi$ could be a sparse matrix such as suggested in, for example, "Compressed Sensing for Real-Time Energy Efficient ECG Compression on Wireless Body Nodes" by Hossein Mamaghanian et al. published in IEEE Transactions on Biomedical Engineering, Volume 58, Number 9, pages 2456-2466, September 2011, the entire contents of which are herein incorporated by reference. Such a sparse matrix consists of a small number of nonzero components in each column, with each column containing at least one nonzero component. The values of nonzero components can be fixed to a constant value, can be selected from two binary values, or can be randomly selected.

Electrocardiogram signals have particular structure which can make them amenable to compressive sensing.

Figure 1A:
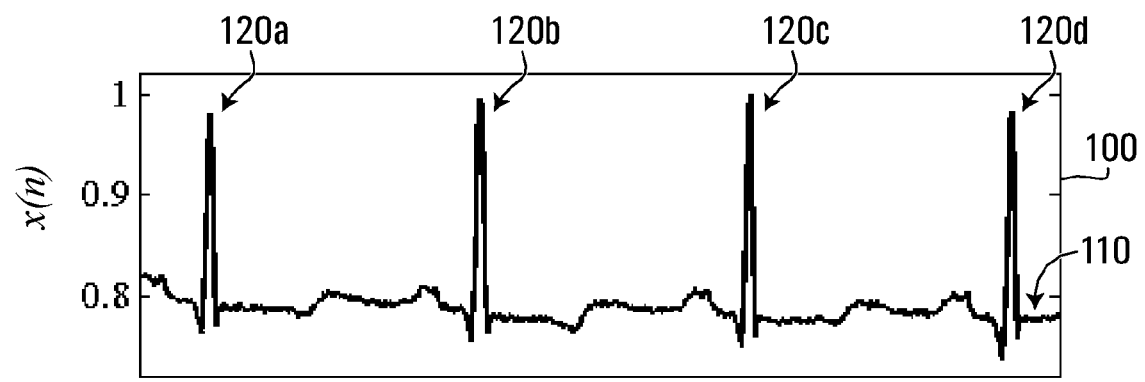
FIG. 1A is an illustration of an ECG signal with transient QRS structures.

FIG. 1A illustrates an example ECG signal. A graph 100 shows a trace of an ECG signal 110. ECG signal 110 has a number of QRS spikes 120a-120d. Notably, the variability of ECG signal 110 in between any two of QRS spikes 120a-d is very low.

A first-order difference $z^d$ of a vector z of length N+1 can be obtained as $$z^d = [z_1^d z_2^d \ldots z_N^d]^T \quad (2)$$

where $z_n^d = z_n - z_{n+1}$ for n=1, 2, . . . , N and $z_n$ is the nth component of z.

Figure 1B:
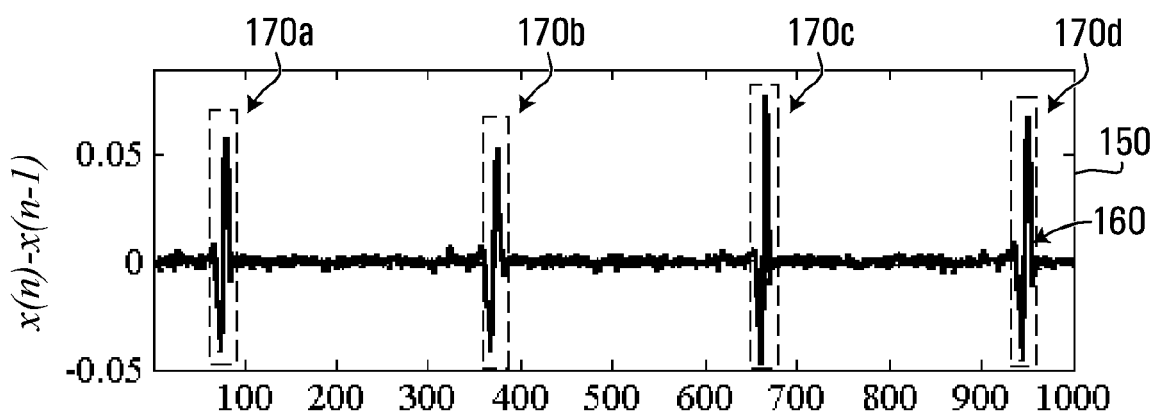
FIG. 1B illustrates the first-order difference of the ECG signal of FIG. 1A.

The first-order difference of the ECG signal 110 of FIG. 1A is shown is FIG. 1B.

Graph 150 shows a first-order difference 160 of ECG signal 110. Notably first-order difference signal 160 has a number of consecutive significant value components 170a-d corresponding to QRS spikes 120a-d of ECG signal 110.

Figure 2:
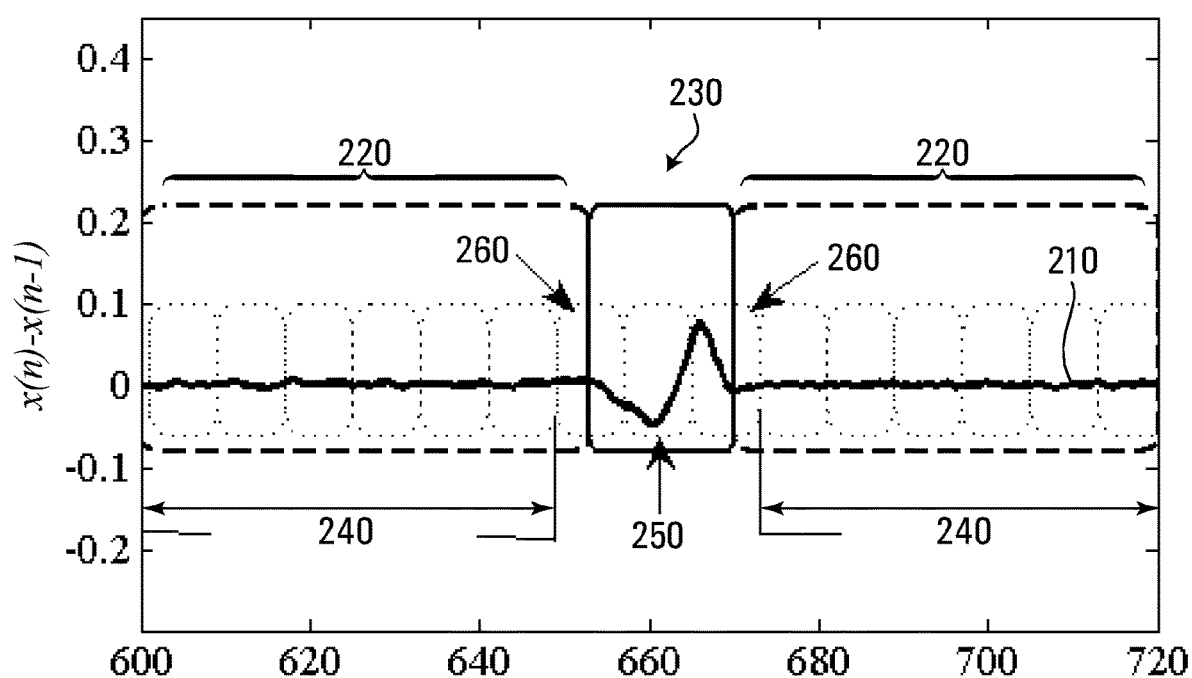
FIG. 2 illustrates the division of the first-order difference vector of an ECG signal into block vectors.

FIG. 2 illustrates how a first-order difference of an ECG signal may be divided into blocks and those blocks may be classified as to whether they are significant or insignificant.

As illustrated, first-order difference signal 210 contains segments 220 of consecutive insignificant value components which may be called insignificant natural blocks and a segment 230 of consecutive significant value components which may be called a significant natural block.

First-order difference signal 210 may also be divided into a number of uniform consecutive block vectors. Those ones of the block vectors falling within an insignificant natural block 220 may be classified as insignificant blocks 240. By contrast, block 250 could fall entirely within significant natural block 230 and may thus be labelled a significant block. Other ones of the consecutive block vectors may span an insignificant natural block and a significant natural block. These block vectors are not desired and thus are labelled as undesired blocks 260.

Having regard to this classification of block vectors within a first-order difference signal, it becomes apparent that the problem of detecting QRS segments is one of finding the indices of significant blocks within the first-order difference signal as the positions of the significant blocks coincide with the positions of QRS segments in the original ECG signal.

Additionally, because the first-order difference vector of ECG signals exhibits this sparsity, ECG signals can be reconstructed from compressively sensed data by encouraging or urging such a block sparse structure over the first-order difference vector of the reconstructed signal during reconstruction. For example, as will become apparent, the $l_{2/p}{}^d$-RLS algorithm can be used to reconstruct an ECG for a chosen block size from a compressively sensed measurement vector y.

The $l_{2/p}{}^d$-RLS algorithm is presented in detail in "Compressive Sensing of Foot Gait Signals and Its Application for the Estimation of Clinical Relevant Time Series" by the inventors which appears in the IEEE Transactions on Biomedical Engineering, vol. 63, no. 7, in July 2016 at pages 1401 to 1415, the contents of which are incorporated herein by reference in their entirety.

Briefly put, in the $l_{2/p}{}^d$-RLS algorithm, suppose b is a positive integer and S=N/b is also a positive integer. A first-order difference vector $a^d$ of length N can be divided into blocks $a_1{}^d, a_2{}^d, \ldots, a_S{}^d$ each of length b (i.e of block size b or, synonymously, into blocks of cardinality b) as $$a^d = [(a_1^d)^T (a_2^d)^T \ldots (a_S^d)^T]^T \quad (3)$$

Then, block-sparsity of $a^d$ can be evaluated by using the $l_{2/p}{}^d$ function $f_r(a)$ given by:

$$f_r(a) = [\Sigma_{n=1}^S (\|a_n^d\|_2)^p]^{1/p} \quad (4)$$

with $0 < p \le 1$.

Consequently, an approximation or estimate of signal x, denoted $x_R$ can be reconstructed from measurement vector y by solving the $l_{2/p}{}^d$—regularized least-squares ($l_{2/p}{}^d$-RLS) problem $$\text{minimize}_{x_R} \tfrac{1}{2}\|\Phi x_R - y\|_2^2 + \lambda f_{r,\in}(x_R) \quad (5)$$

where the regularization function $f_{r,\in}(a)$—which is a smoothed approximation of the function $f_r(a)$ in Equation (4)—is given by $$f_{r,\epsilon}(a) = \sum_{i=1}^{S} \left(\|a_i^d\|_2^2 + \epsilon^2\right)^{p/2}, \quad (6)$$

with $0 < p \le 1$.

Equation (5) includes a regularization parameter $\lambda$. Regularization parameter $\lambda$ can be used to balance the trade-off between the block-sparse structure and signal fidelity. A small value of $\lambda$ is suitable for the fidelity of reconstructed signal for satisfying Equation (1). A large value of $\lambda$ is suitable for enforcing block-sparse structure on the first-order difference vector $a^d$ at the cost of signal fidelity.

Equations (5) and (6) also both utilize a parameter $\in$ which holds a small positive value and can be used to facilitate the optimization by making the function $f_{r,\in}(a)$ smooth.

Optimal values of each of regularization parameter $\lambda$ and parameter $\in$ may be determined using iterative techniques such as through trial and error.

In an example, $\{\lambda \approx 0.1, \in \approx 10^{-2}, p=1\}$ has been found to be effective for attaining reasonable fidelity for ECG signals whose amplitude is normalized to unity.

Notably, for the enhancement of transient structure of QRS complex, a sufficient large value of $\lambda$ and sufficient small value of $\in$ can facilitate urging or enforcement of a block sparse structure.

Equation (6) also utilizes a non-zero parameter p having a value of at most 1. A very small value of p, $0 < p < 0.1$, may enhance transients in QRS structure. However, as with $\lambda$ and $\in$, whether a particular value of p is appropriate is application dependent. Accordingly, routine experimentation, such as using trial and error could be used to find suitable values of p, $\lambda$, and $\in$ for particular applications.

In an example, $\{\lambda \approx 10^8, \in \approx 10^{-10}, p=10^{-5}\}$ has been found to be suitable for enforcing block-sparse structure on the first-order difference of ECG signals whose amplitude has been normalized to the unity value.

When reconstructing compressively sensed ECG signals using the $l_{2/p}{}^d$—RLS algorithm, undesired blocks such as those illustrated in FIG. 2 may occur if the start time of the significant natural block does not coincide with one of the signal blocks and/or if the end time of a significant natural block does not coincide with the end time of one of the signal blocks. Because there is no guarantee that the signal blocks will be temporally aligned with the locations of the natural blocks in the original ECG signal, undesired blocks can occur for at least a small number of significant natural blocks during signal reconstruction.

Notably, such undesired signal blocks can be expected to cause error in the reconstruction of any adjoining significant natural block. As a result, any significant natural blocks in the original signal that are significantly impacted by undesired signal blocks may tend to be suppressed in the reconstructed signal.

Conveniently, the $l_{2/p}{}^d$-RLS algorithm can be made more robust by running it independently for a variety of different block sizes and by then computing an average reconstructed signal.

The results of reconstruction may also be further improved by performing post-processing on the various reconstructed signals prior to the averaging operation.

Figure 3:
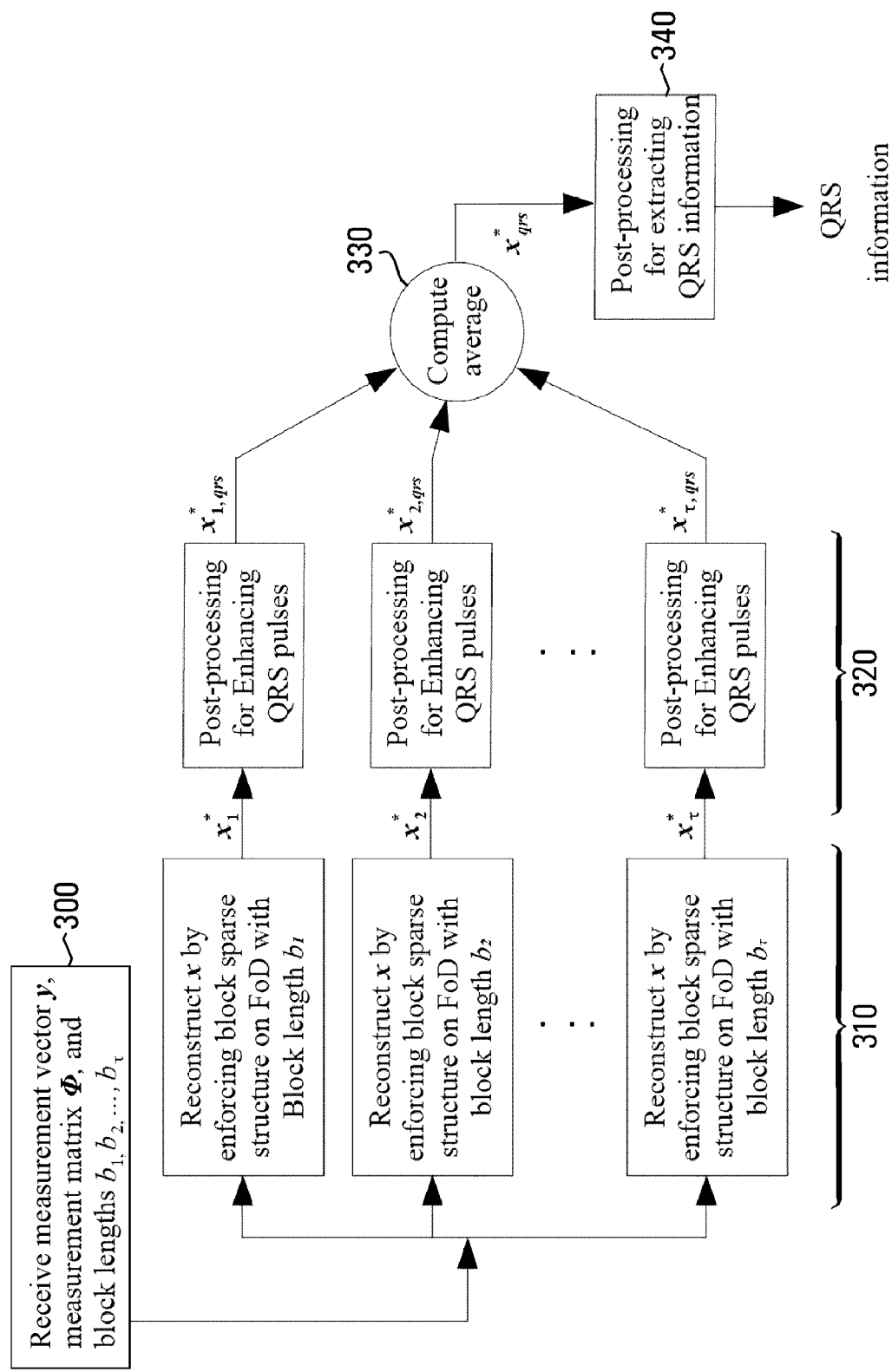
FIG. 3 is a functional block diagram of a technique for extracting QRS information from compressively sensed ECG data.

FIG. 3 is a functional block diagram of a technique for extracting QRS information from compressively sensed ECG data at a receiver.

As illustrated, at block 300, a measurement vector y is received as input. Measurement vector y corresponds to a signal vector x that was compressed into measurement vector y using measurement matrix $\phi$ according to equation (1). Measurement matrix $\phi$ is also taken as input to block 300 along with various block lengths $b_1, b_2 \ldots b_T$. Various block lengths $b_1, b_2 \ldots b_T$ are well chosen to be closely spaced.

In some embodiments, block lengths may not be received but may instead be predefined constants or may be selected programmatically.

In other embodiments, a constant value of block length b is supplied with a set of T shift values associated with block edges.

Additionally or alternatively, values of block lengths (b) may be estimated using suitable techniques, such as, for example through the application of machine learning, computational techniques, or combinations thereof.

In some embodiments, the division of a signal into blocks of a given block size may result into a division into blocks having cardinality that is approximately, rather than exactly equal, to the specified block size.

More particularly, in some embodiments, the size of blocks may be allowed to vary from the specified block size within specified limits. For example, the length of blocks could be allowed to vary from the specified length by one sample, plus or minus. This may allow a first-order difference vector of a length that is not an even multiple of the specified block size to be divided into blocks by distributing the remainder samples across the various blocks. Conveniently, in this way, any error resulting from having a single short block holding the remainder samples may be distributed across the various blocks.

In a particular example, given a first-order difference vector $z^d$ of length N can be divided into blocks of lengths $b_1, b_2, b_3, \ldots, b_s$ where $b_i \cong b \forall i$, $1 \leq i \leq s$, as $$z^d = [\tilde{z}_1, \tilde{z}_2, \tilde{z}_3 \ldots \tilde{z}_S]^T \qquad (7)$$

Blocks $\tilde{z}_1, \tilde{z}_2, \tilde{z}_3 \ldots \tilde{z}_S$ are defined by block-edge indices $1, n_{b_1}, n_{b_2}, n_{b_3}, \ldots, n_S$ where $$n_{b_i} = \tilde{b} \times i \qquad (8)$$

for $i=1, 2, \ldots, S$ where $$S = \left\lfloor \frac{N}{b} \right\rfloor \qquad (9)$$

and $$\tilde{b} = \left\lfloor \frac{N}{S} \right\rfloor \qquad (10)$$

As set out above, the first block-edge index can be manually selected to fall at position 1 (i.e. the first sample) in $z^d$. The last index $n_S$ is then necessarily equal to N.

As set out above, the maximum difference between the desired block length b and the approximate block length $\tilde{b}$ may be controlled. For example, for N>400, the maximum difference between b and $\tilde{b}$ may be 1 sample. In another example, for 400>N>300, the maximum difference between b and $\tilde{b}$ may be 2 samples. In yet another example, for 200>N>300, the maximum difference between b and $\tilde{b}$ may be 3 samples. Notably, N>400 may be desirable in compressive sensing of ECG signals. In such embodiments, therefore, the maximum difference between b and $\tilde{b}$ may be 1 sample.

Additionally or alternatively, in some embodiments, the block boundaries may intentionally offset by a specified value. For example, the first block may be made longer or shorter than the other blocks by a number of samples less than or greater than such a specified intended block shift time value. Necessarily such a block shift time cannot exceed the desired block length b.

Of course, a skilled person will recognize that the use of non-uniform blocks may necessitate that all block-wise processing respects block edges $1, n_{b_1}, n_{b_2}, n_{b_3}, \ldots, n_S$, rather than assuming a uniform block length $\tilde{b}$.

At block 310, ECG signal x is reconstructed from y by enforcing block sparse structure on the first-order difference for each of the chosen blocks. In some embodiments, this may be done for each or some of the block lengths in parallel with each or some of the other block lengths. Reconstruction may be done using the $l_{2/p}^d$—RLS algorithm (i.e. according to equation (5)), though it is not required. For example, in alternative embodiments, reconstruction may be done using another suitable algorithm for reconstructing measurements from compressively sensed data that enforces or urges a block sparse structure on the first-order difference.

At block 320, post-processing is performed on each of the reconstructed ECG signals. The post-processing is intended to enhance the QRS formations in the reconstructed signal prior to the averaging operation. In alternate embodiments, this post-processing may be omitted. However, omitting post-processing could reduce the performance of the overall QRS information extraction.

At block 330, the average of each of the post-processed reconstructed signals is computed. The average may be computed as a simple arithmetic mean of each of the corresponding entries of the various post-processed reconstructed vectors. Alternatively, the average may be a weighted average, wherein the components of the vectors coming from the sub-blocks in block 320 are multiplied with weight-values before computing the arithmetic mean. In such a weighted average, the components of a vector coming from a sub-block in block 320 may be multiplied by a constant weight or may alternatively be multiplied by different weight values.

The values of the weights, whether constant or different, may be obtained using various techniques. In some embodiments, values for weights may be selected using computational techniques. For example, computation techniques could be utilized to select weights based on the expected characteristics of the signal. Additionally or alternatively, weights may be adaptively updated such as, for example, through application of machine learning techniques.

Notably, the output of block 330 represents the output of the reconstruction algorithm. This output may then be post-processed at block 340 to determine the positions/timings of the QRS complexes in the original ECG signal.

Figure 4:
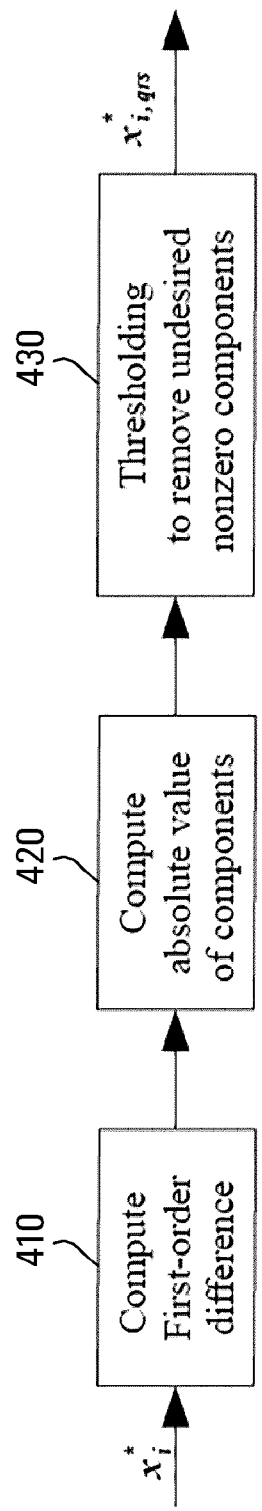
FIG. 4 is a simplified functional block diagram illustrating post-processing blocks for enhancing QRS pulses in reconstructed ECG data.

FIG. 4 is a simplified functional block diagram illustrating example post-processing blocks for enhancing QRS pulses in reconstructed ECG data, such as may be performed at block 320 at a receiver.

In the example post-processing illustrated in FIG. 4, each of the reconstructed signals for the various block sizes undergo several signal processing blocks intended to improve the quality of the resulting average signal.

At block 410, the first-order difference of a reconstructed signal is computed such as, for example, according to equation (2).

At block 420, the absolute value of the components of the first-order difference signal is determined. Then, at block 430, a thresholding operation is applied to remove undesired non-zero components from the signal.

The absolute value at block 420 is computed simply by computing the absolute value of each entry in the first-order difference signal.

At block 430, the thresholding operation simply compares each entry in the absolute value signal to a threshold value to determine whether it is greater than the threshold. Values less than the threshold in the output will be set to zero and values greater than the threshold will be passed through unchanged.

In some embodiments, the threshold value will be a constant. Alternatively, the threshold value could be selected programmatically based on properties of the reconstructed signal, the first-order difference signal, or the absolute value signal.

Figure 5:
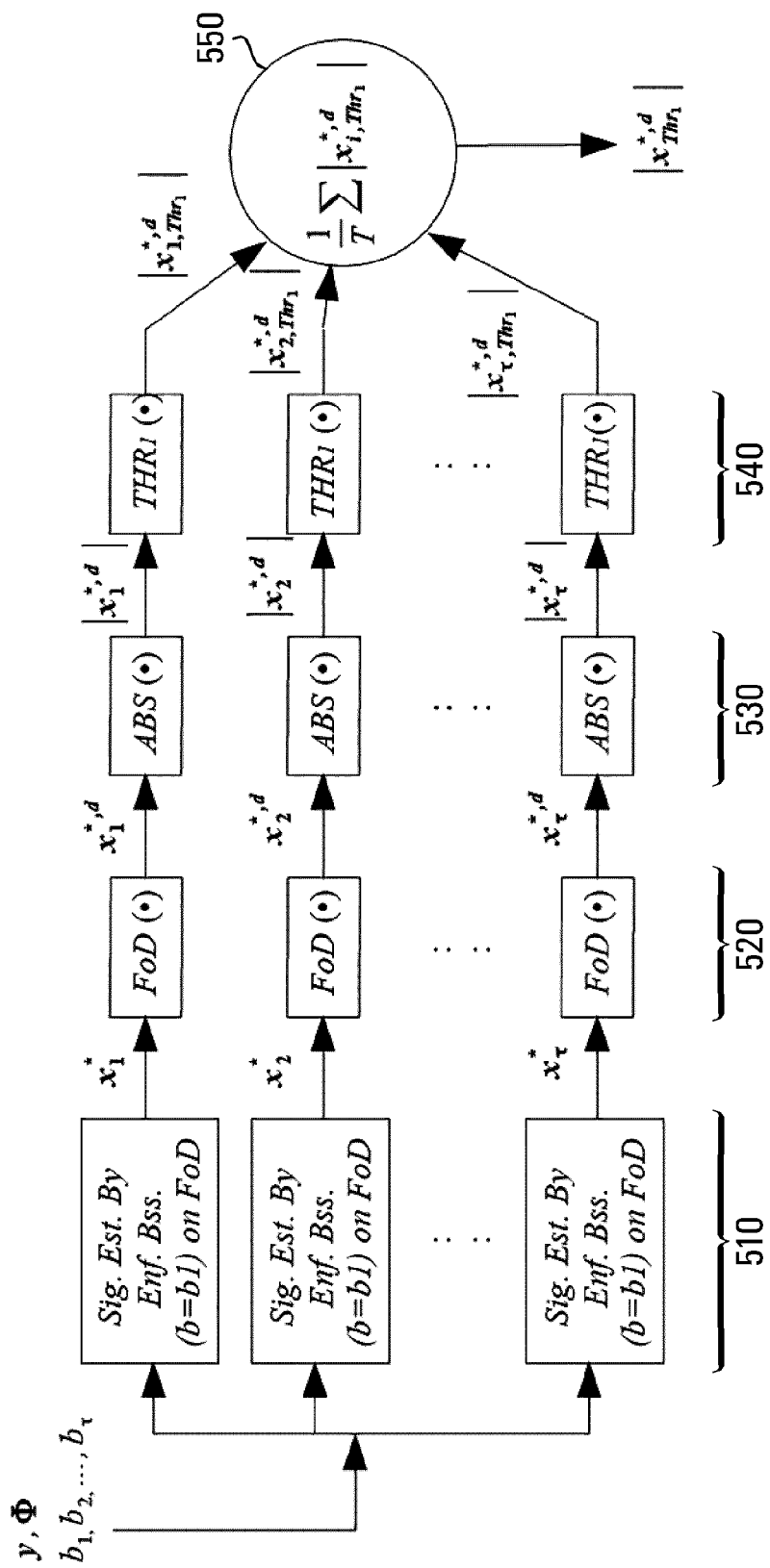
FIG. 5 is a functional block diagram of an exemplary technique for reconstructing ECG data from compressively sensed measurements and post-processing for enhancing QRS pulses in reconstructed data.

FIG. 5 is a functional block diagram of an exemplary technique for reconstructing ECG data from compressively sensed measurements and post-processing for enhancing QRS pulses in reconstructed data.

As illustrated, in some embodiments, each of the blocks in the reconstruction of the enhanced first-order difference signal may be performed in parallel. Alternatively, one or more of the operations at each block may be performed sequentially in various order such as may be apparent to skilled persons.

For example as discussed above, signal estimation for various block sizes at block 510 may be performed in parallel or in series. Similarly, computation of the first-order difference at block 520, computation of absolute values of the first-order difference signals at block 530, and computation of thresholded signals at block 540 may be performed in series or in parallel so long as no operation is performed until any necessary input values for that operation have been computed.

Finally, once all of the thresholded values have been computed, an enhanced first-order signal is generated via an averaging operation at block 550.

Figure 6:
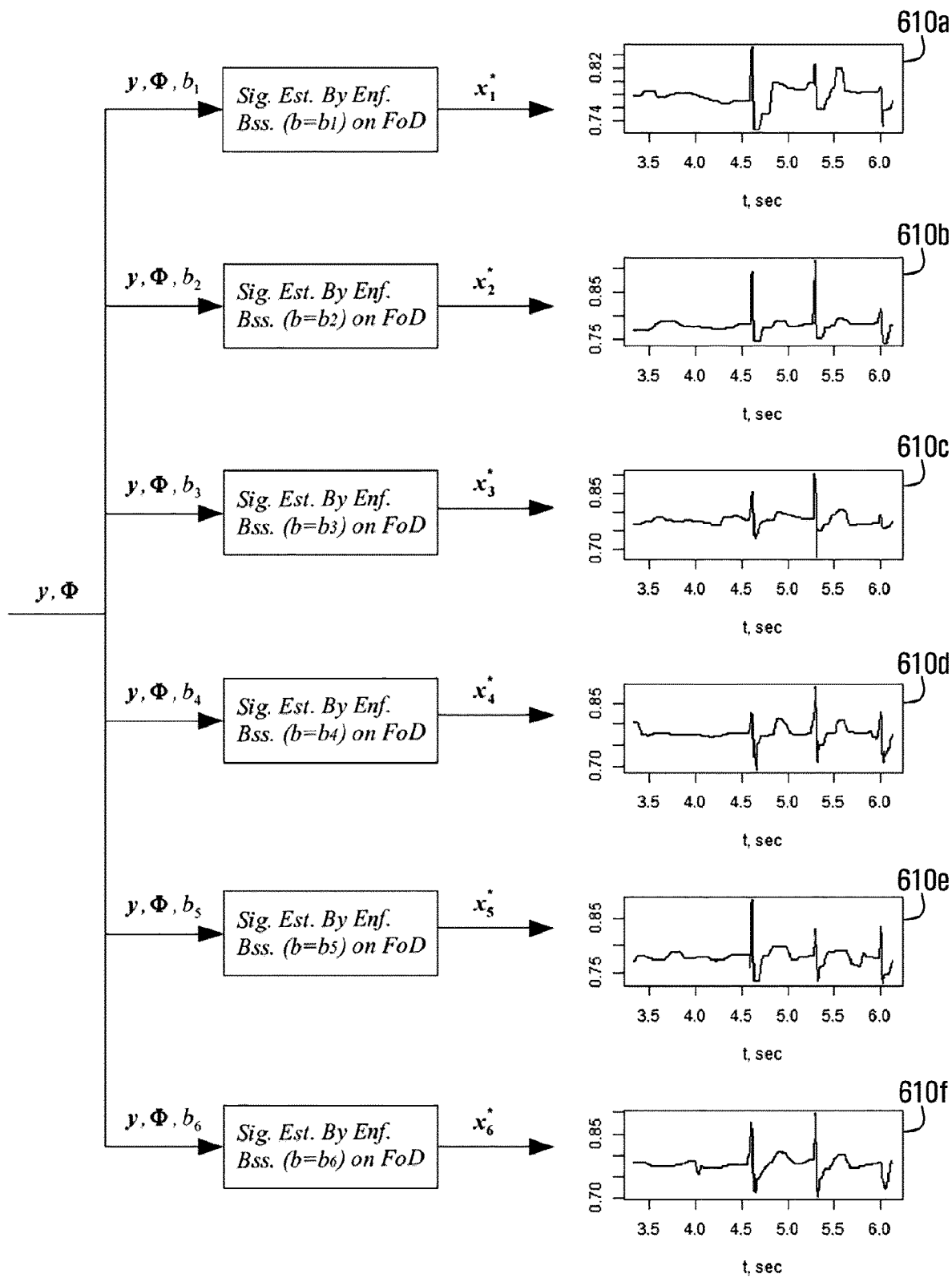
FIG. 6 illustrates signals reconstructed by enforcing block sparse structure for a variety of block sizes on the first-order difference when processing compressively sensed ECG data.

FIG. 6 illustrates signals reconstructed by enforcing block sparse structure for a variety of block sizes on the first-order difference when processing compressively sensed ECG data.

As illustrated, by performing signal estimation for a variety of block sizes, a plurality of reconstructed signals 610a through 610f may be generated such as, for example, using the $l_{2/p}^d$-RLS algorithm as described above. These signals may then be used as the input to the post-processing prior to averaging as discussed above.

Figure 7:
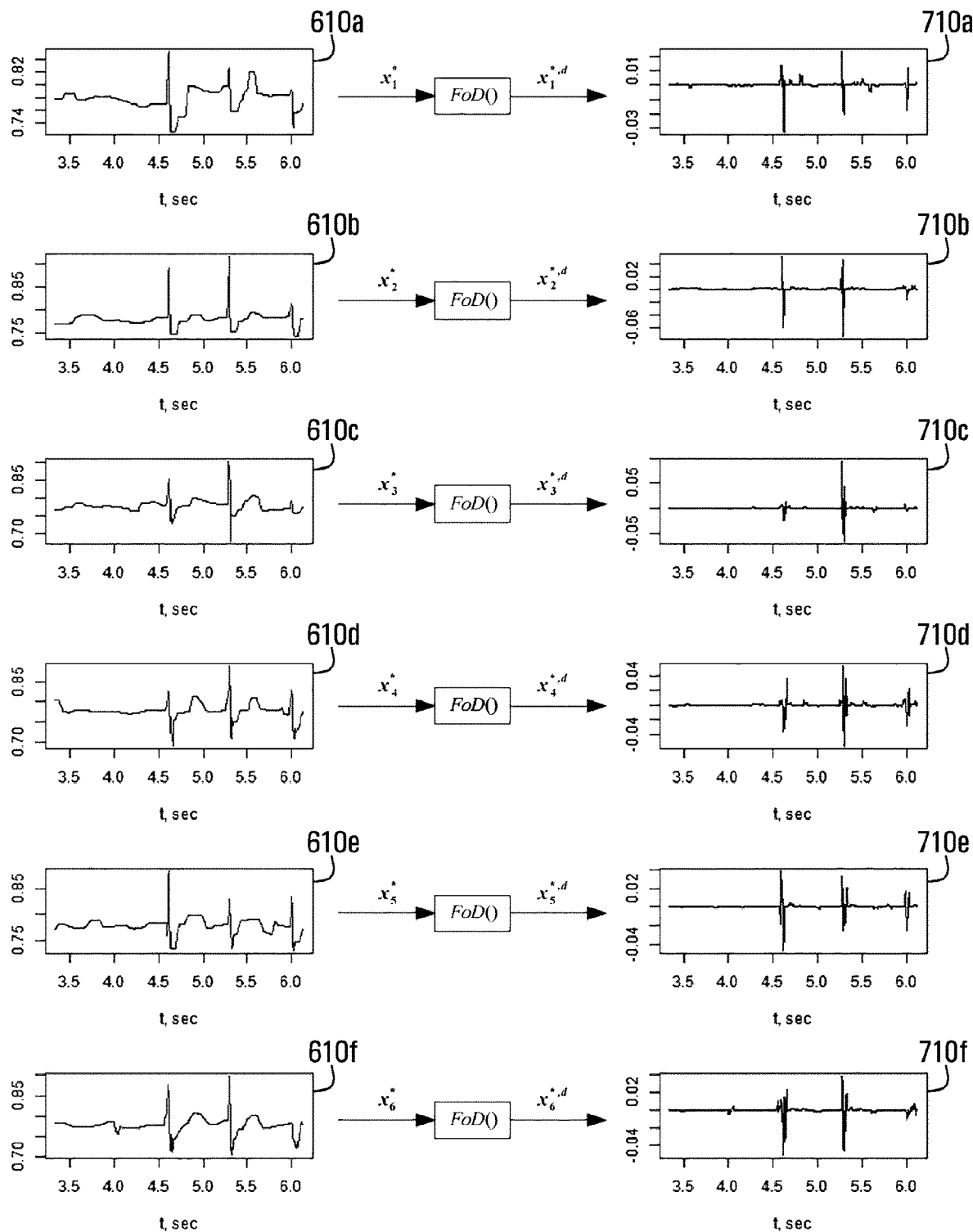
FIG. 7 illustrates first-order difference vectors obtained by applying a first-order difference operation on each of the example ECG segments of FIG. 6.

FIG. 7 illustrates first-order difference vectors obtained by applying a first-order difference operation on each of the example ECG segments of FIG. 6.

As illustrated, each of the reconstructed ECG signals 610a through 610f is subjected to a first-order difference operation (as described above) resulting in corresponding first-order difference signals 710a through 710f, respectively.

Figure 8:
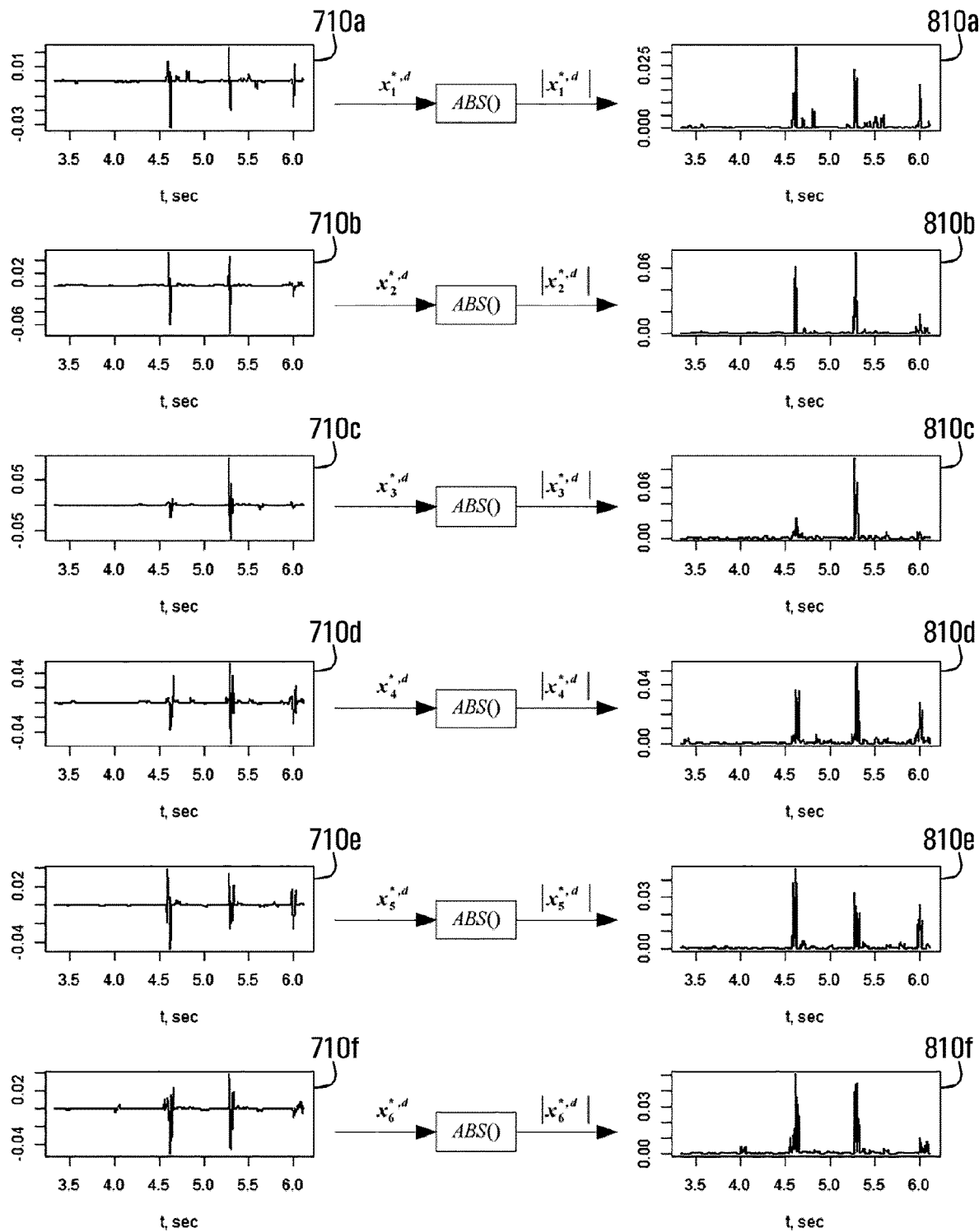
FIG. 8 illustrates vectors obtained by applying the absolute operator to example vectors of FIG. 7.

FIG. 8 illustrates vectors obtained by applying the absolute operator to example vectors of FIG. 7.

As illustrated, each of first-order difference vectors 710a to 710f is subjected to an absolute value operation resulting in absolute value first-order difference vectors 810a through 810f.

Figure 9:
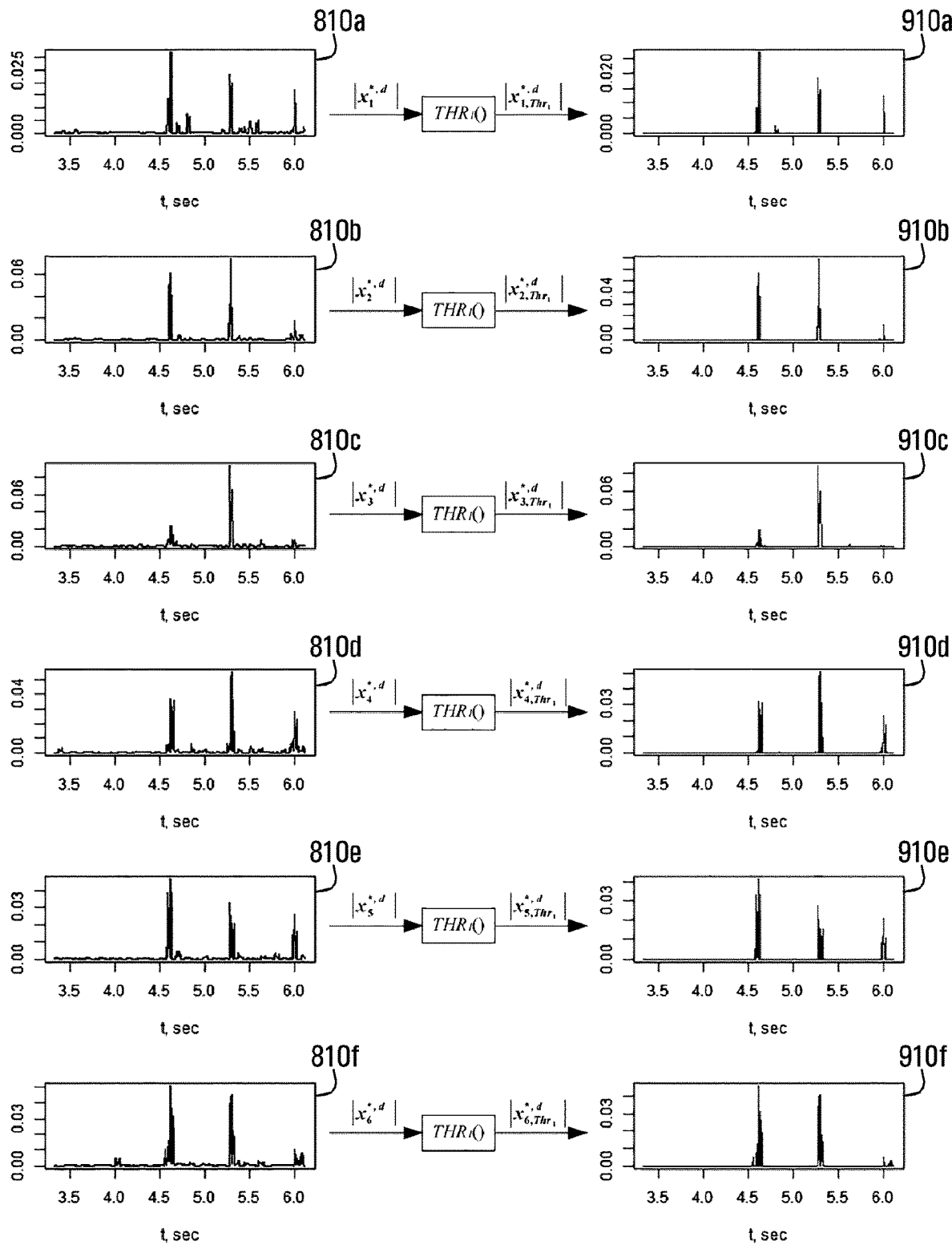
FIG. 9 illustrates vectors obtained by applying a threshold operator to result vectors from FIG. 8.

FIG. 9 illustrates vectors obtained by applying a threshold operator to result vectors from FIG. 8.

As illustrated, each of absolute value first-order difference vectors 810a through 810f is subjected to a thresholding operating (as described above) resulting in thresholded absolute value first-order difference vectors 910a through 910f. Notably, each of thresholded absolute value first-order difference vectors 910a through 910f exhibits fewer low power transient components as compared to the corresponding ones of absolute value first-order difference vectors 810a through 810f.

Figure 10:
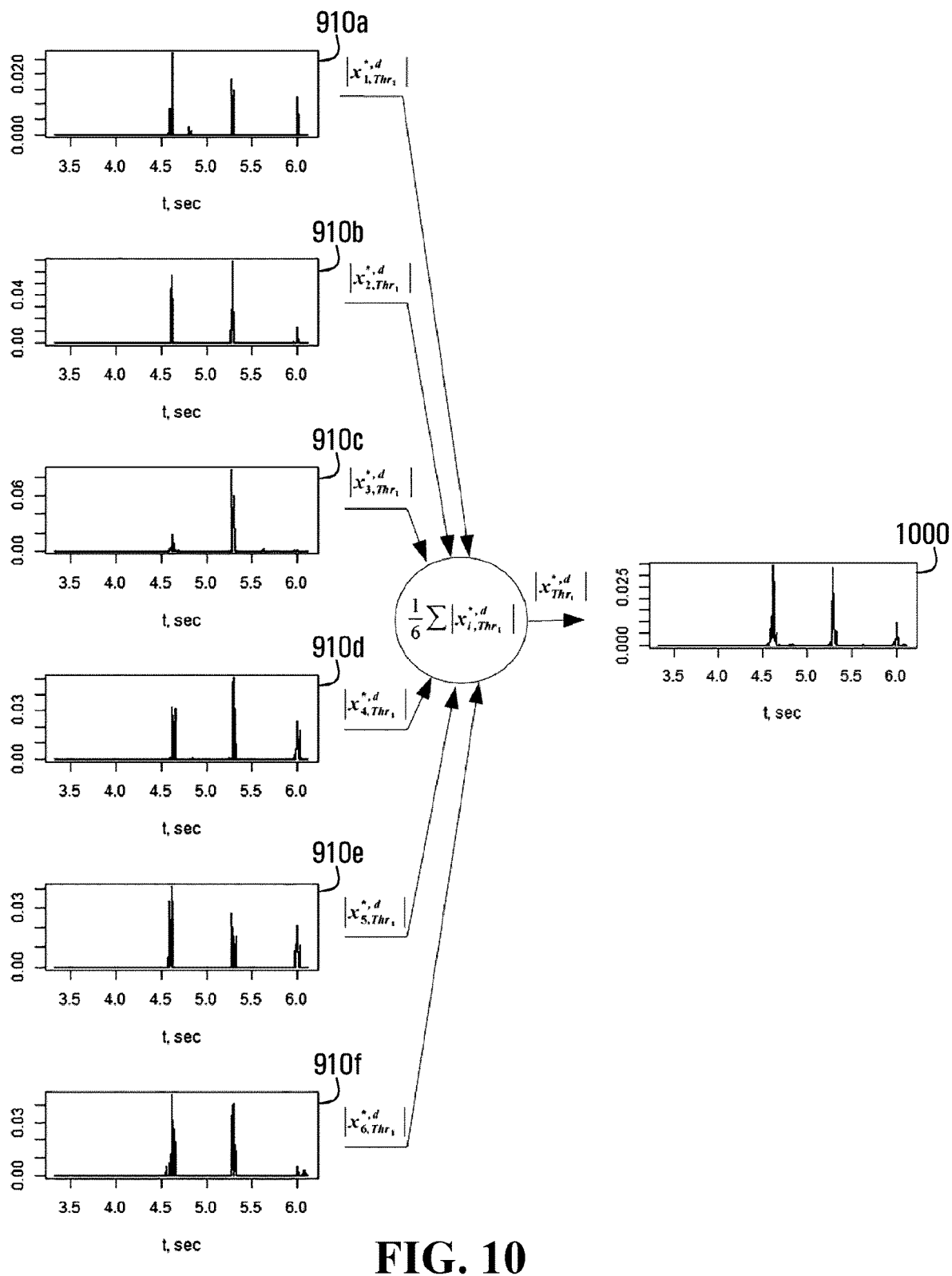
FIG. 10 illustrates how an enhanced first-order difference vector may be obtained by averaging result vectors from FIG. 9.

FIG. 10 illustrates how an enhanced first-order difference vector may be obtained by averaging result vectors from FIG. 9.

As illustrated, each of thresholded absolute value first-order difference vectors 910a through 910f is averaged together as described above to produce an enhanced first-order difference vector 1000. Notably, enhanced first-order difference vector 1000 exhibits clear block sparse structure.

Returning to FIG. 3, once an enhanced first-order difference vector has been generated, it may be subjected to post-processing to detect QRS complexes at block 340 of that figure.

Figure 11:
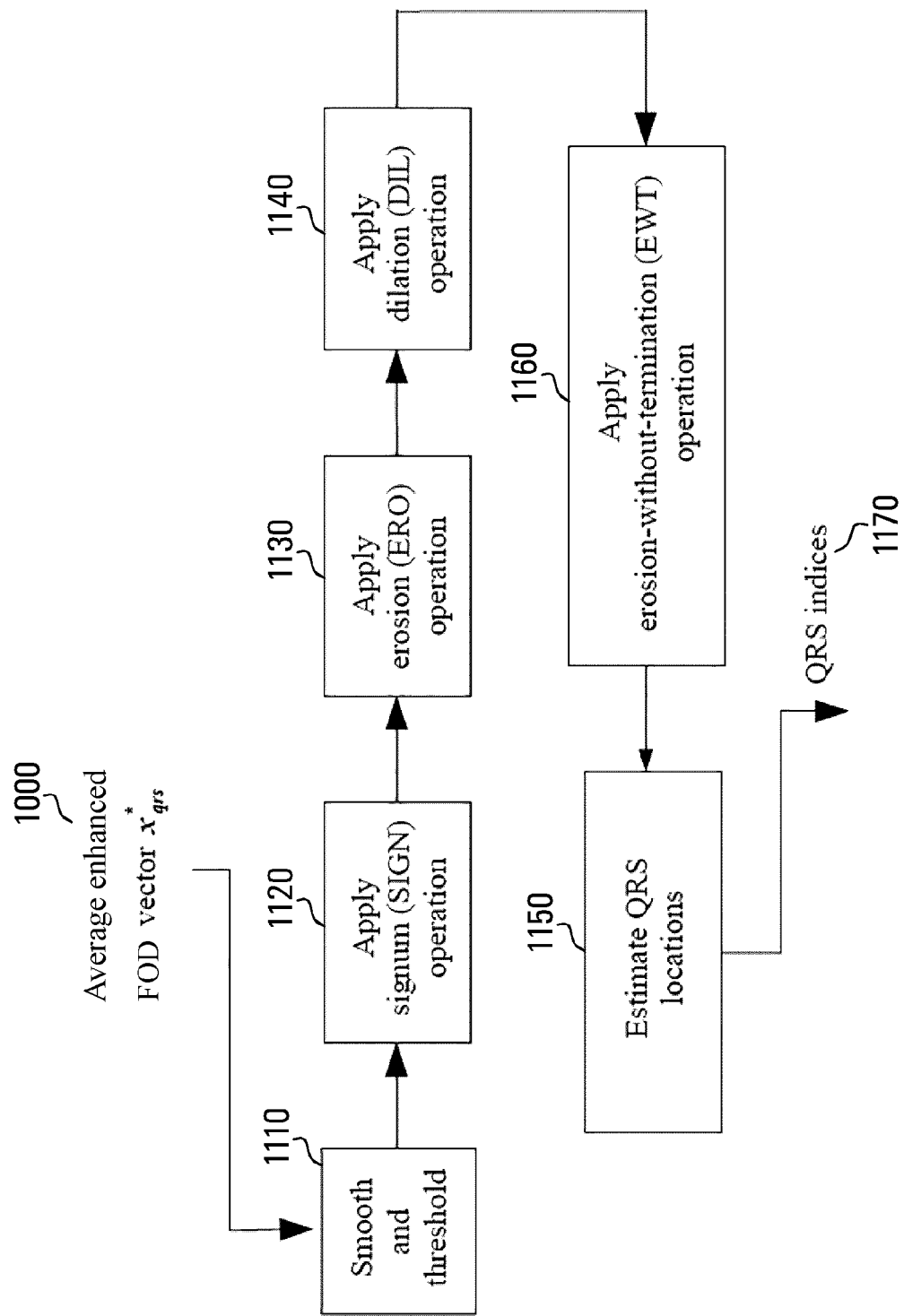
FIG. 11 is a functional block diagram of an example technique for post-processing an enhanced first-order difference vector to thereby determine locations of QRS complexes in the corresponding originally sensed ECG signal.

FIG. 11 is a functional block diagram of an example technique for post-processing an enhanced first-order difference vector to thereby determine locations of QRS complexes in the corresponding originally sensed ECG signal.

As illustrated, average enhanced first-order difference vector 1000 may be subjected to a number of analysis blocks in order to determine the location of significant blocks. In a first block, average enhanced first-order difference vector 1000 is subjected to a smooth and threshold operation 1110. Next, a signum operation 1120 is applied. Then, an erosion operation 1130 is applied to the output of the previous operation. Next, a dilation operation 1140 is applied to the output of the erosion operation 1130. Then, an erosion-without-termination operation 1160 is applied to the output of the dilation operation 1140. At this point, the signal may then be analyzed to determine estimated locations of QRS complexes at block 1150 resulting in detected QRS indices 1170.

The details of exemplary ones of each of the aforementioned operations will be described in turn, with reference to example input and output signals illustrated in FIGS. 12-17.

Smooth and threshold operation 1110 comprises two blocks: first, average enhanced FoD (first-order difference) vector 1000 is subjected to a smoothing operation.

The smoothing operation may be a suitable low-pass filter. For example, a low-pass moving average filter with suitable length or order may be utilized for smoothing. For example, in some embodiments, a low-pass moving average filter or length or order may be utilized for smoothing.

Figure 12:
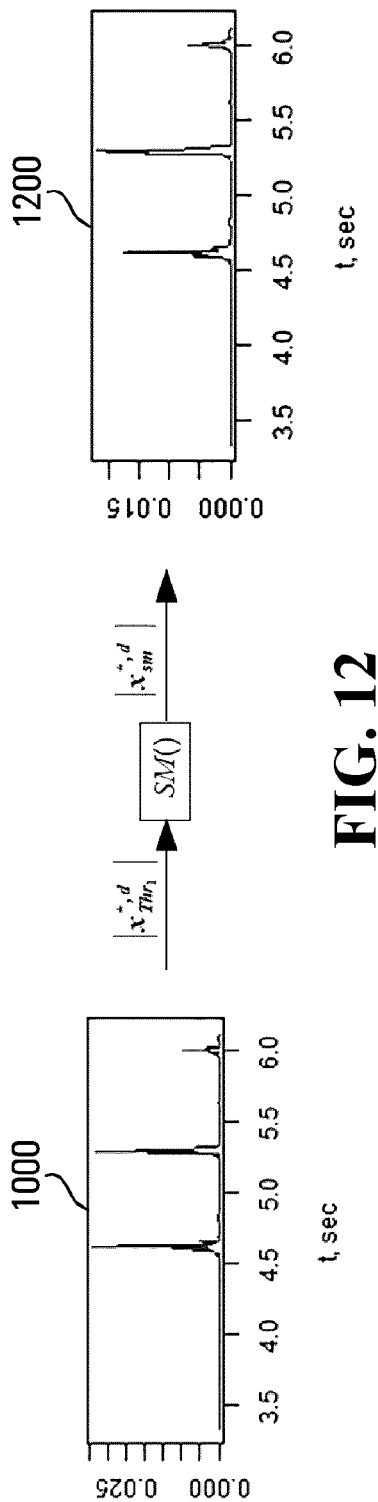
FIG. 12 illustrates the result of applying a smoothing operation to an example enhanced first-order difference vector.

FIG. 12 shows an output vector 1200 resulting from application of the smoothing operation to example enhanced FoD vector 1000.

Then, following smoothing, the resultant signal vector is subjective to a thresholding operation, where values in the vector are compared to a small positive threshold value and only values greater than that threshold are passed through, with all other values being instead clamped to zero. In some embodiments, the threshold applied to each entry in the vector may be identical. Alternatively, threshold values may be chosen for various parts of the signal such as, for example, based on characteristics of the ECG signal.

Following the smooth and threshold operation, a signum operation is applied to the resultant signal vector. Signum operation 1120 returns one for a given value in its input if that value is non-zero and, otherwise, returns a zero value. In other words, any entry of non-zero value is set to 1 while zero values simply pass through.

Figure 13:
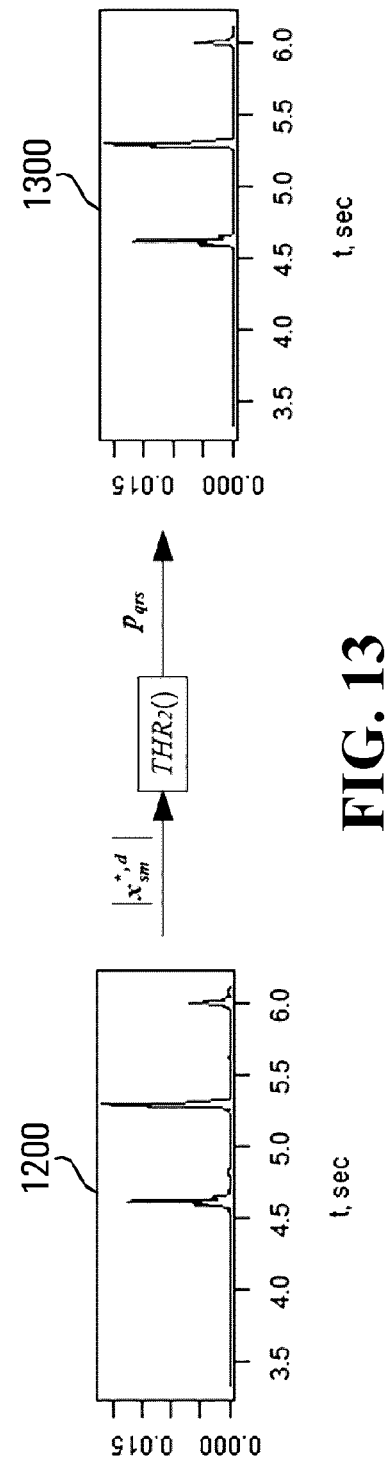
FIG. 13 illustrates the result of applying a thresholding operation to the smoothed enhanced first-order difference result vector in FIG. 12.

FIG. 13 shows an example output vector 1300 resulting from application of the threshold operation to smoothed vector 1200.

Figure 14:
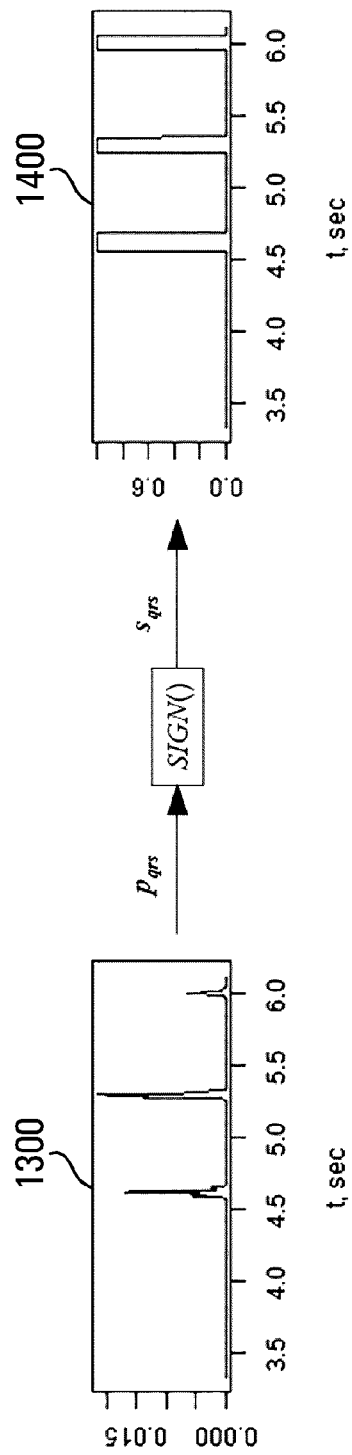
FIG. 14 illustrates the result of applying a signum operation to the result vector of FIG. 13.

FIG. 14 shows an example output vector 1400 resulting from application of the signum operation to thresholded vector 1300.

Notably, considered together, the thresholding and signum operation result in values less than the threshold being forced down to zero and values greater than the threshold being clamped to 1. Values equal to the threshold may result in either 0 or 1, the choice between the two being an implementation detail of various embodiments.

In some embodiments, the thresholding and signum operations may be combined into a single block.

The output of the signum operation is then used as input to erosion operation 1130 (ERO). Erosion operation 1130 may be applied several times.

Figure 15:
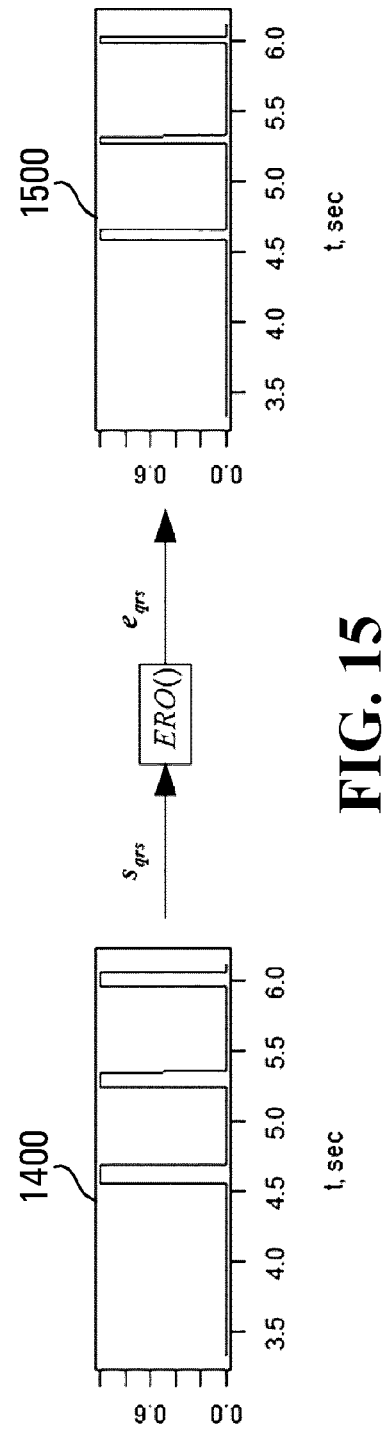
FIG. 15 illustrates the result of applying an erosion operation to the result vector of FIG. 14.

FIG. 15 shows an example output vector 1500 resulting from repeating the application of the erosion operation to vector 1400 several times.

As illustrated, the erosion operation is applied to vector 1400. Notably, by way of the erosion operation, the first and last components of each rectangular pulse in the vector are set to zero. More particularly, by repeating this process for several times, undesired rectangular pulses, which are usually of a small duration, and/or impulses are removed.

In some embodiments, erosion operation 1130 may be based on a numeral 3-component moving maximum window. For example, erosion operation may yield the vector given by $$u_{sm}^{er} = [u_{sm,1}^{er} u_{sm,2}^{er} \ldots u_{sm,N}^{er}]^T \quad (11)$$

for an input $u_{sm}$ where $$u_{sm,i}^{er} = \begin{cases} u_{sm,i} & \text{for } i = 1/N \\ u_{sm,i}^{mmn} & \text{otherwise} \end{cases} \quad (12)$$

and where $u_{sm,i}^{mmn}$ is 3-component moving minimum, which can be obtained as $$u_{sm,i}^{mmn} = \min\{u_{sm,i-1}, u_{sm,i}, u_{sm,i+1}\} \quad (13)$$

for i=2, 3, . . . , N–1.

Returning to FIG. 11, following erosion operation 1130, the output thereof may be passed to dilation operation 1140 (DIL). Dilation operation 1140 may be based on a numeral-3 component moving maximum.

Figure 16:
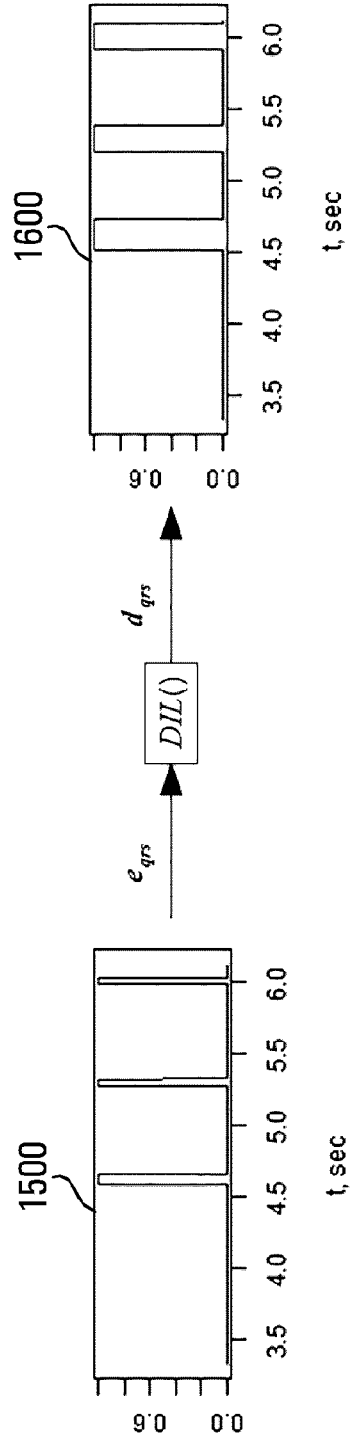
FIG. 16 illustrates the result of applying a dilation operation to the result vector of FIG. 15.

FIG. 16 shows an example output vector 1600 resulting from several applications of the dilation operation to eroded vector 1500.

Notably, by way of the dilation operation, the zero valued components adjoining each rectangular pulse in the vector are set to one. Conveniently, by repeating the dilation operation several times, rectangular pulse erroneously divided into multiple pulses may be rejoined together to form a single rectangular pulse.

In some embodiments, the dilation operation may yield a vector $u_{sm}^{dl}$ given by $$u_{sm}^{dl} = [u_{sm,1}^{dl} u_{sm,2}^{dl} \ldots u_{sm,N}^{dl}]^T \quad (14)$$

for an input $u_{sm}$ where $$u_{sm,i}^{dl} = \begin{cases} u_{sm,i} & \text{for } i = 1, N \\ u_{sm,i}^{mmx} & \text{for } i = 2, \ldots, N-1 \end{cases} \quad (15)$$

and $u_{sm,i}^{mmx}$ is the 3-component moving maximum computed as $$u_{sm,i}^{mmx} = \max\{u_{sm,i-1}, u_{sm,i}, u_{sm,i+1}\} \quad (16)$$

for i=2, 3, . . . , N–1.

In some embodiments, the order of erosion operation 1130 and dilation operation 1140 may be interchanged. Additionally or alternatively, a given signal may be subject to multiple rounds of one or both of erosion operation 1130 and dilation operation 1140.

Several rounds of dilation operation 1140 may have the effect of merging small rectangular pulses in the input that could have formed from the splitting of a desired unit rectangular pulse across multiple blocks during signal reconstruction. Meanwhile, one or more rounds of erosion operation 1130 may eliminate undesired small-size unit rectangular blocks. Ultimately, through combined application of erosion operation 1130 and dilation operation 1140, a vector containing rectangular pulses at locations of QRS segments may result.

Finally, the output of the erosion and dilation operations is subjected to a further erosion-with-termination (EWT) operation 1160.

In some embodiments, EWT operation can be applied on the vector $u_{sm}$ to obtain the vector $u_{sm}^{ewt}$ as $$u_{sm}^{ewt} = [u_{sm,1}^{ewt} u_{sm,2}^{ewt} \ldots u_{sm,N-1}^{ewt}]^T \quad (17)$$

for an input $u_{sm}$ where $$u_{sm,i}^{ewt} = \begin{cases} u_{sm,i} & \text{for } i = 1, N \\ \max\{u_{sm,i}^{(1)}, u_{sm,i}^{(2)}\} & \text{for } i = 2, \ldots, N-1 \end{cases} \quad (18)$$

and where $u_{sm,i}^{(1)}$ and $u_{sm,i}^{(2)}$ are 3-component moving minimum and 3-component impulse flag index, respectively, which can be obtained as $$u_{sm,i}^{(1)} = \min\{u_{sm,i-1}, u_{sm,i}, u_{sm,i+1}\} \quad (19)$$

$$u_{sm,i}^{(2)} = \min\{1 - u_{sm,i-1}, u_{sm,i}, 1 - u_{sm,i+1}\} \quad (20)$$

for i=2, 3, . . . , N–1.

Figure 17:
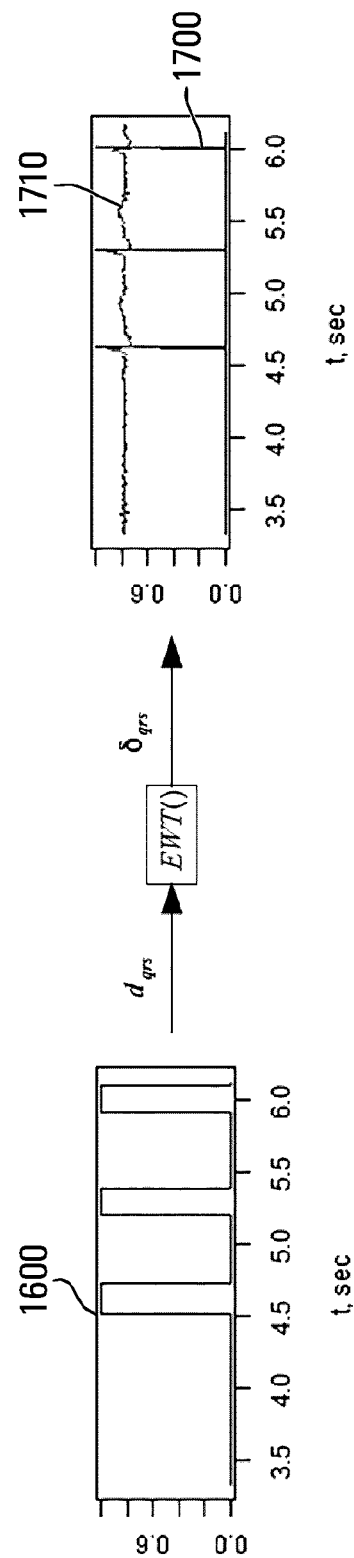
FIG. 17 illustrates the result of applying an erosion without termination (EWT) operation to the result vector of FIG. 16.

FIG. 17 shows a QRS impulse vector 1700 resulting from application of the EWT operation to dilated vector 1600.

In some embodiments, the EWT operation comprises a further repetitive application of the EWT operation whereby the EWT operation is applied until only a signal impulse remains at the location of any rectangular pulse. In other words, the EWT operation leaves a single pulse at the locations of rectangular pulses.

More particularly, a skilled person will recognise that where a single application of the EWT operation removes only the first and last components from a block of consecutive unity value components, the application of sufficient large number of EWT operations will have the effect of removing all but components except impulses (i.e., blocks with only one unity value component) from its input signal.

In some embodiments, other signal pulse estimate techniques may be substituted for or may supplement the repeated application of the EWT operation. For example, in some embodiments, signals pulse locations may be estimated using computational techniques, such as, for example, by computing the edge-indices of rectangular pulses and then computing a mean of the edge-indices to determine an approximate location for a corresponding pulse.

As discussed above, each of the dilation, erosion, and EWT operations may be repeated for a suitable number of times. The suitable number of repetitions for each dilation, erosion, and EWT operations may depend on the particular application scenario for the techniques disclosed herein as well as on other factors such as, for example, signal morphology. In some embodiments, techniques such as for example, trial and error and various machine learning techniques may assist in estimating suitable numbers of iterations to apply for the various operations.

For example, 10 repetitions of the erosion operations and 25 repetitions of the dilation operation were found to result in suitable outputs for various experiments on example ECG data.

Original ECG signal vector 1710 is overlaid on the graph of QRS impulse vector 1700 for comparison. Notably, each of the impulse peaks in QRS impulse vector 1700 corresponds to a QRS complex in original signal ECG vector 1710 showing how the locations of QRS complexes in the original ECG signal vector 1710 have been detected by the above described processing.

In order to compare the above-described technique employing the above-described technique to known $l_{2/p}^d$-RLS signal reconstruction algorithm, the inventors conducted a Monte Carlo experiment where an example ECG segment was compressed at various compression ratios—specifically, 80%, 85%, 90%, 91%, 92%, 93%, 94%, 95%, and 96%—using random sparse measurement matrices.

In particular, for each compression ratio, the following steps were repeated one hundred times:
 a. Creating a random sparse measurement matrix $\phi$,
 b. Computing measurements y of the example ECG segment x using the measurement matrix $\phi$,
 c. Applying an embodiment of the novel processing techniques described above to the compressed measurements to obtain a QRS impulse vector, and
 d. Applying the $l_{2/p}^d$-RLS algorithm followed by first-order difference, absolute value, and threshold operations plus the post-processing operations shown in FIG. 11 to obtain a second QRS impulse vector.

Figure 18:
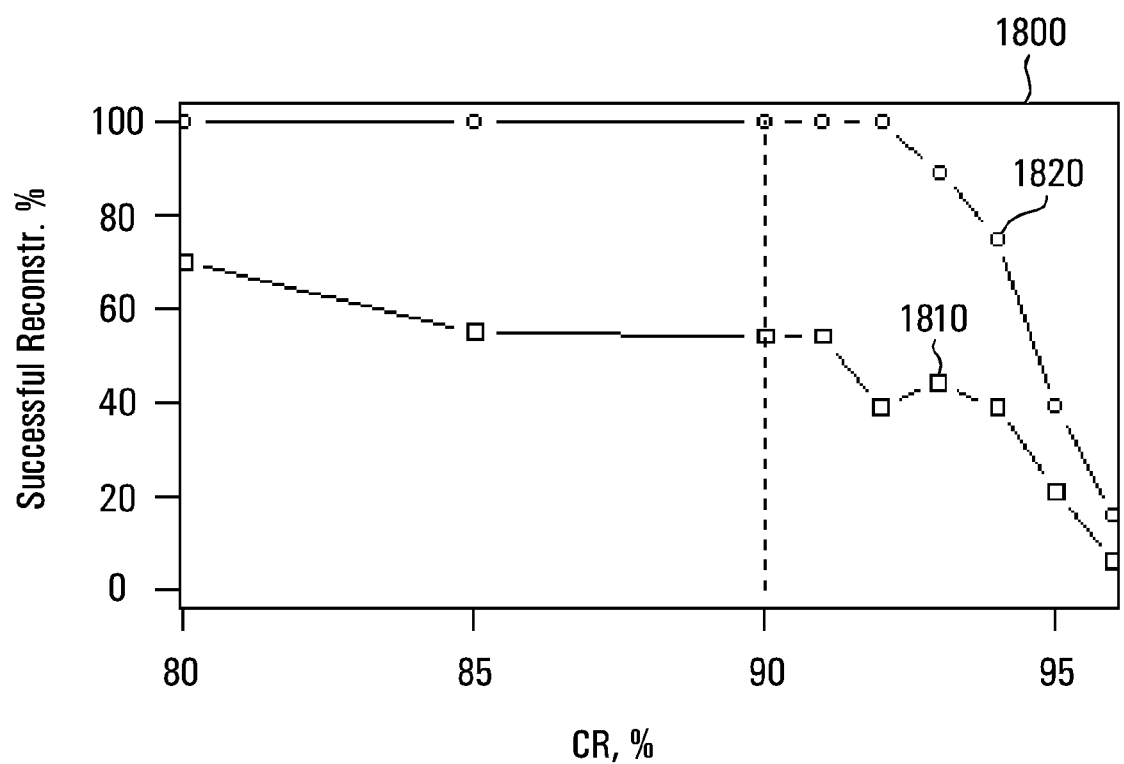
FIG. 18 is a graph showing performance of the disclosed technique as compared to known techniques on compressively sensed ECG data for various compression ratios.

The accuracy of the locations in the resulting QRS impulse vectors were then compared to the locations of QRS complexes in the original ECG signal segment, where segment length was set to N=1024. The percentage of the reconstruction instances for which the impulse locations were accurate with respect to the QRS locations over the reconstruction of thousand different segments is illustrated in FIG. 18.

As shown in graph 1800, performance of the above-described techniques (curve 1820) resulted in perfect detection for compression ratios up to 92%. By contrast, the block sparsity on first-order difference algorithm from step d (curve 1810) was not able to achieve successful reconstruction even half the time at any compression ratio in excess of 90% during the Monte Carlo experiment.

Accordingly, the above-described techniques may allow use of high compression ratio compressive sensing while still permitting QRS segment locations to be detected in the compressed signal.

In some embodiments, the above described techniques, can also be used for enhancing robustness of CS-based QRS detection in conjunction with known QRS detection algorithms, such as, for example, the Pan-Tompkins algorithm. In effect, a known QRS detection algorithm may be applied to reconstructed ECG data to locate QRS complexes, instead of using the above described post-processing for determining locations of QRS complexes. In such embodiments, ECG data is still reconstructed from compressively sensed measurements in similar fashions to those already described above. For example, signals may still be reconstructed for a variety of block sizes and then averaged. In some such embodiments, post-processing for enhancing the QRS complexes may be omitted. For example, referring to FIG. 5, one or more of blocks 520, 530, 540 could be omitted.

The performance of a given algorithm in detecting QRS complexes can be measured using an index representative of the proportion of correctly detected QRS complexes with a penalty for false alarms. As such, a Correct Detection Index (CDI) gives a measure of accuracy in the detection of QRS complexes while considering false alarms.

For example, a CDI can be defined as $$CDI_{[*]} = 2 \times (\alpha \cdot HT - (1-\alpha) \cdot FA) \quad (21)$$

where $0 < \alpha < 1$.

In equation (21), HT (hits) denotes the percentage of correctly detected QRS complexes as compared to the total number of true QRS complexes and FA (false alarms) denotes the percentage of wrongly detected QRS complexes with respect to the total number of true QRS complexes.

The parameter $\alpha$ is a weighting parameter where $\alpha = 0.5$ corresponds to CDI=HT−FA.

Figure 19:
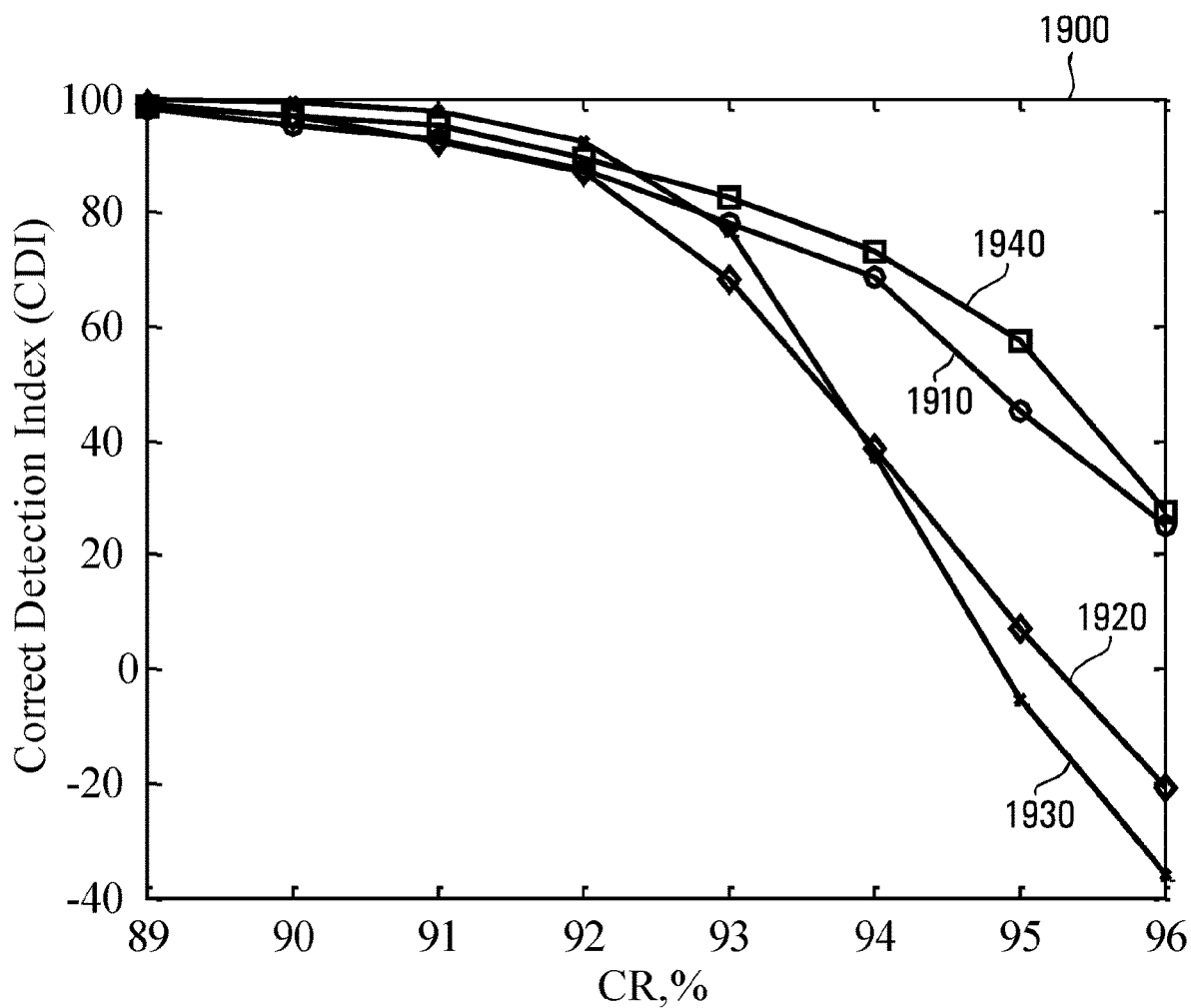
FIG. 19 is a graph showing performance of a hybrid technique for various compression ratios.

FIG. 19 is a graph illustrating the performance of various hybrid techniques combining a known QRS detection algorithm, namely the Pan-Tompkins algorithm, with various variations on the above described techniques for reconstructing ECG data from compressively sensed measurements.

To generate each of the curves in graph 1900, ECG signals were reconstructed using a parallel structure for reconstruction as described above whereby the $l_{2/p}^d$-RLS algorithm was applied for a variety of block sizes with the resultant outputs combined through averaging to yield a constructed signal.

The $l_{2/p}^d$-RLS was applied in two modes: a first mode favouring sparsity, $l_{2/p}^d$-RLS-SPR, with $\lambda=400$, p=0.01, and a second mode enforcing SNR, $l_{2/p}^d$-RLS-SNR, with $\lambda=1$, p=1. In each case, post-processing for enhancing the QRS complexes was not performed. In other words, neither the FoD operator, the absolute operator, nor the threshold operator was applied to the estimated signal for a given block size prior to averaging. Following the averaging operation, the averaged signal was supplied to the Pan-Tompkins algorithm and the resulting QRS detection was scored using the CDI of equation (21).

The performance of the combination of reconstruction by $l_{2/p}^d$-RLS-SPR and $l_{2/p}^d$-RLS-SNR together with the Pan-Tompkins algorithm for compressively sensed measurements with various compression ratios is illustrated by curves 1910 and 1920 respectively.

For comparison, the ECG signal was also constructed from compressively sensed measurements using the $l_p^d$-RLS algorithm described in "Reconstruction of ECG signals for compressive sensing by promoting sparsity on the gradient" by the inventors which appears in the Proceedings of the IEEE International Conference on Acoustics, Speech and Signal Processing at pages 993-997 in May 2013, the contents of which are incorporated herein by reference in their entirety. The output of the $l_p^d$-RLS algorithm was then supplied as input to the Pan-Tompkins algorithm and the performance of the resulting ECG detection for various compression ratios is illustrated by curve 1930.

Finally, the $l_{2/p}^d$-RLS as described above, including parallel signal reconstruction for various block sizes (as illustrated in, e.g. FIG. 5) without the use of post processing, i.e., without blocks 520, 530, and 540, was used in combination with the Pan-Tompkins algorithm. Such processing may allow comparison with curves 1910, 1920, and 1930. The performance of the resulting ECG detection for various compression ratios is illustrated by curve 1940.

As can be seen, performance of the algorithm described above including the post-processing for determining locations of QRS complexes (curve 1940) is better than that for the other algorithm, at higher compression ratios, with the difference becoming particularly marked at ratios approaching 96%. In other words, the $l_{2/p}^d$-RLS algorithm in conjunction with parallel signal reconstruction for various block sizes (as described above) is the best performer for CS-based QRS detection with extremely high compression ratio.

Figure 20:
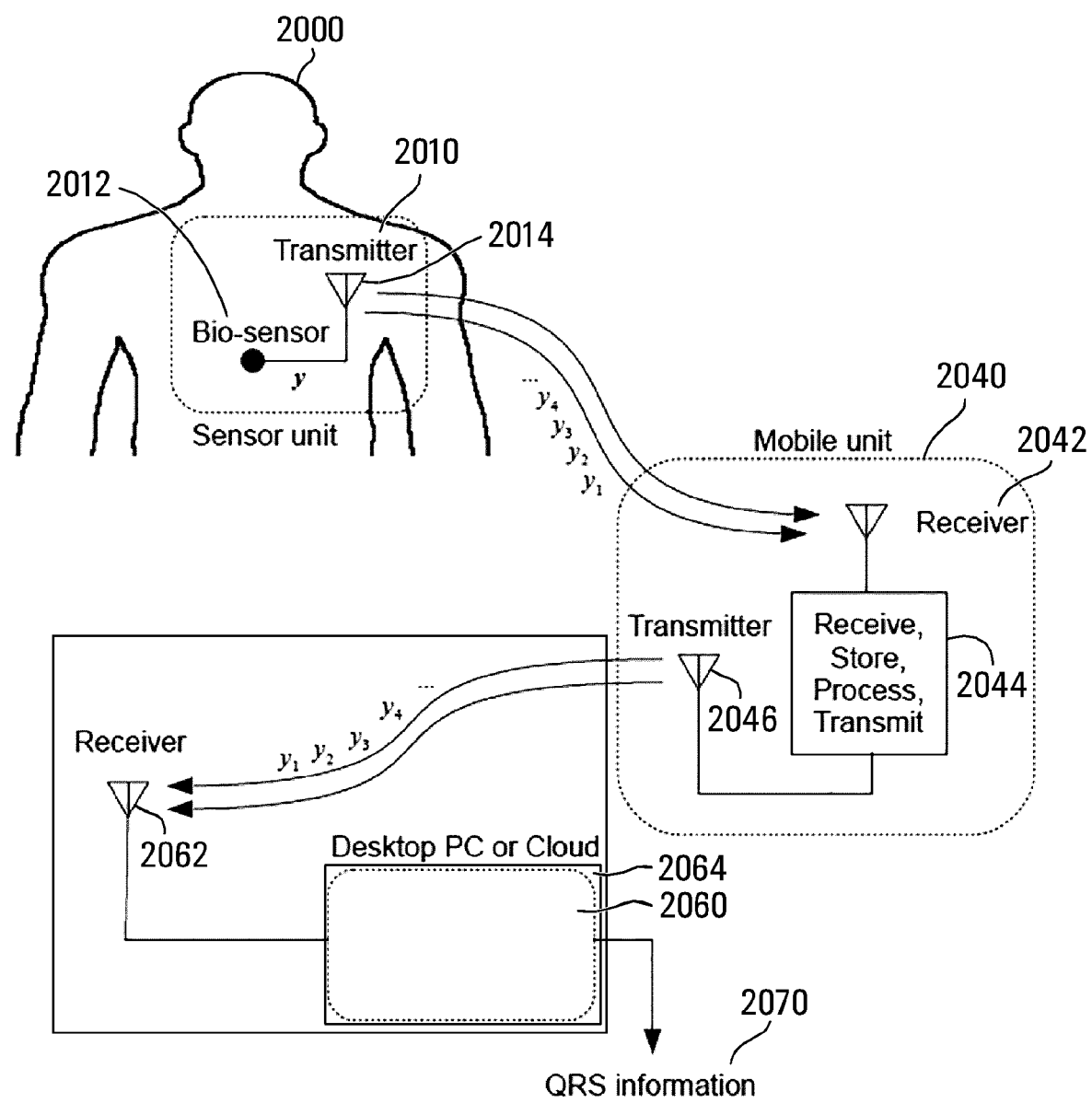
FIG. 20 illustrates an example application scenario for a technique for QRS detection or estimation.

The above described techniques may be used in a variety of applications. FIG. 20 illustrates an example application scenario for a technique for QRS detection or estimation.

As illustrated, a sensor unit 2010 is connected to a human body 2000 such as, for example, using ECG leads as they may typically be connected to a human body in electrocardiography.

Sensor unit 2010 is in communication with a mobile unit 2040 placed nearby, i.e., within 1 to 10 meters of the human body.

Mobile unit 2040 is then in communication with a reconstruction unit 2060 which may be located within a short distance of the human body such as, for example, 10 meters or so, so that reconstruction unit 2060 is able to receive data from mobile unit 2040.

Sensor unit 2010 includes a biosensor 2012 and a transmitter 2014. Biosensor 2012 may comprise hardware suited for receiving ECG signals, such as may be known to persons skilled in the art. For example, biosensor unit 2012 may comprise one or more ECG leads, amplifiers, analog-to-digital convertors (ADCs) etc.

Biosensor unit 2012 is in communication with a transmitter 2014. Transmitter 2014 is adapted to communicate data from sensor unit 2010 to mobile unit 2040. For example, transmitter 2014 may transmit using a suitable low power and short distance wireless technique as may be known to persons skilled in the art. For example, transmitter 2014 may transmit using an ANT+, low energy (LE) Bluetooth, etc. Notably, each of the aforementioned techniques may be configured to transmit data within the aforementioned range of 10 meters.

Since data is received at mobile unit 2040 by way of receiver 2042, receiver 2042 is selected to go along with transmitter 2014 so that they may communicate using a compatible protocol. In some cases, each of transmitter 2014 and receiver 2042 will be adapted to use a single same protocol. Alternatively, one or both of transmitter 2014 and receiver 2042 may be adapted to communicate using more than one protocol or technique, and one or both of transmitter 2014 and receiver 2042 may comprise logic suited for selecting or negotiating a common protocol for communication therebetween. In some embodiments, mobile unit 2040 may process the received data using receiver processor 2044. Alternatively, mobile unit 2040 may simply retransmit the received data using another protocol. In the case, data is transmitted from mobile unit 2040 onward to reconstruction unit 2060 by way of a transmitter 2046. In some embodiments, such as, for example, where reconstruction unit 2060 is within a short distance (i.e. less than 10 meters) of mobile unit 2040 a low power and short distance wireless technique such as, for example, ANT+ or LE Bluetooth may be used for transmitting from mobile device transmitter 2046 to reconstruction unit receiver 2062. Alternatively, such as, for example, when reconstruction unit 2060 is located further away from mobile unit 2040, an alternate protocol such as, for example, Bluetooth™ or WiFi™ (e.g. 802.11a, b, g, n or the like) may be utilized.

Of course the above description of transmission and reception is by no means limiting. In some embodiments, connections may be by way of one or more permanent or intermittent wire connections. For example, one or more sensor unit 2010 and mobile unit 2040 may buffer measurements for a later transmission, such as, for example, when the units come into range of each other or, when a wired connection is established therebetween. In other embodiments suitable connection techniques may employ a mobile network such as, for example, a cellular data unit using a suitable protocol such as for example, GPRS, HSPA, or LTE.

As described above, data is received at reconstructed unit 2060 by way of a receiver 2062. The received data is then passed to an appropriate unit such as a desktop PC 2064, so that it may be analyzed to identify QRS complexes such as by way of the above-described techniques resulting in QRS information 2070. For example, a process (e.g. a CPU) of desktop PC 2064 may execute software comprising instructions and stored in a computer-readable storage medium such as, for example, a magnetic disk, optical storage, or the like. Execution of the instructions by the processor may cause the desktop PC to analyze the received data, such as by way of the above-described techniques, resulting in QRS information 2070. Of course, this is by no means limiting and other appropriate units and techniques may be employed as would be apparent to persons skilled in the art.

Figure 21:
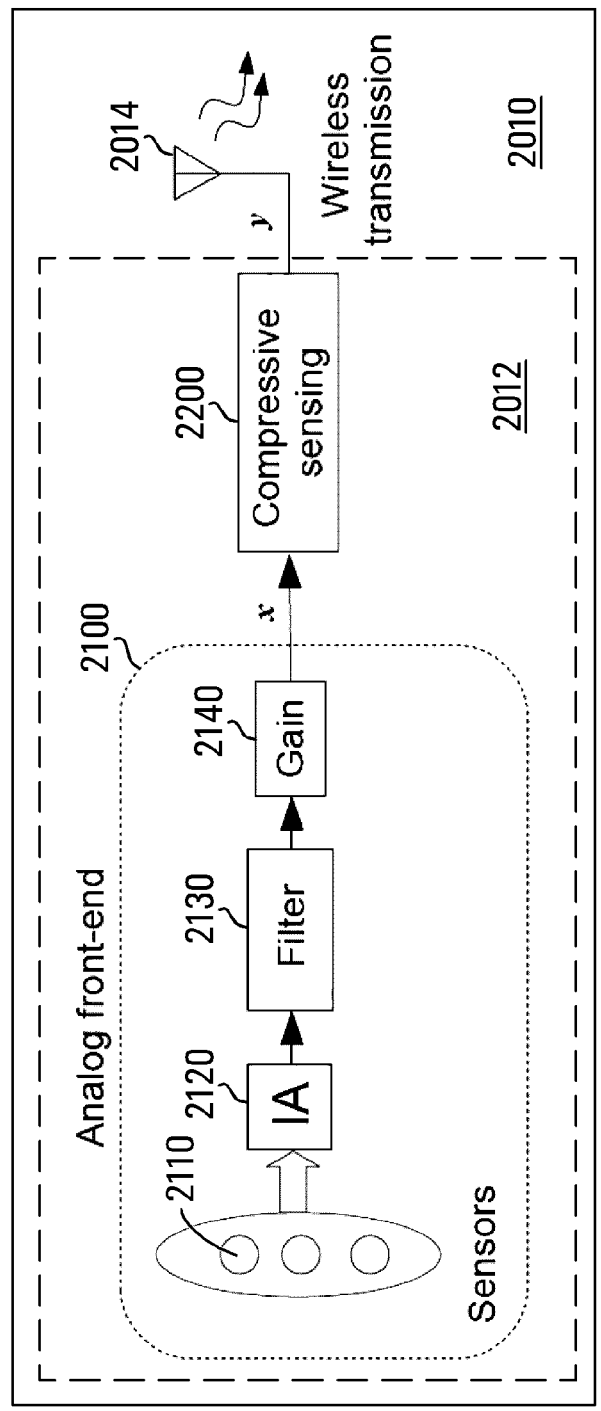
FIG. 21 is a block diagram of an example sensor unit as may be employed for compressively sensing ECG data.

FIG. 21 is a block diagram illustrating an example sensor unit 2010.

As illustrated, biosensor unit 2012 may include an analog front-end portion 2100 and a compressive sensing portion 2200.

In analog front-end portion 2100, one or more sensors 2110 collect data from human body 2000 (not shown). The output of one or more sensors 2110 is then forwarded to an instrumentation amplifier 2120 and then onward to filter 2130 and to gain control 2140.

Analog filter 2130 is used to remove three components of the signal: (a) components of frequency smaller than 0.1 Hz, (b) components of frequency greater than 250 Hz, and (c) 60 Hz (or 50 Hz, depending on the location) powerline interference. Filtering low frequencies helps to remove baseline wander, motion related artifacts, and any signal drift. Filtering out higher frequency components helps to remove out-of-band noise from the signal. For example, analog filter 2130 may comprise a bandpass filter for the range 0.1-250 Hz and a 60 Hz notch filter.

The output from analog front-end 2100 may be converted to a digital signal using an analog-to-digital convertor (ADC). The output from the ADC forms a sequence of samples which may then be supplied to compressive sensing unit 2200. The output of compressive sensing unit 2200, a series of compressed measurements, is then transmitted onward to the mobile unit 2040 by way of transmitter 2014 as discussed above.

In some embodiments, the ECG signal coming out of instrumentation amplifier 2120 may nominally range from 100 uV to 4 mV, with the range being further reduced after the signal passes through filter 2130.

To convert voltage in such ranges into digital signal an 8 bit ADC may be suitable. As known to skilled persons, by employing a 9, 10 or greater bit ADC, improved Signal-to-Noise Ratios (SNR) may be achieved due to a reduction in quantization noise. The use of a higher bit ADC may require additional amplification prior to the input of the filtered signal into the ADC.

Gain control 2140 can be used to adjust the range of the analog ECG signal supplied to ADC.

In some embodiments, analog front-end 2000 may be as described in "An Analogue Front-End System with a Low-Power On-Chip Filter and ADC for Portable ECG Detection Devices" by Shuenn-Yuh Lee, Jia-Hua Hong, Jin-Ching Lee, and Qiang Fang appearing as chapter 16 of the book "Advances in Electrocardiograms—Methods and Analysis" edited by Richard M. Mills, published Jan. 25, 2012 by INTECH, the contents of the entirety of which are herein incorporated by reference.

In other embodiments, an analog front-end may be such as described in "Compressed sensing analog front-end for bio-sensor applications" by D. Gangopadhyay, E. G. Allstot, A. M. R. Dixon, K. Natarajan, S. Gupta, and D. J. Allstot published in IEEE Journal on Solid-State Circuits, vol. 49, no. 2, at pages 426-438 in February 2014, the contents of which are herein incorporated by reference in their entirety.

Figure 22:
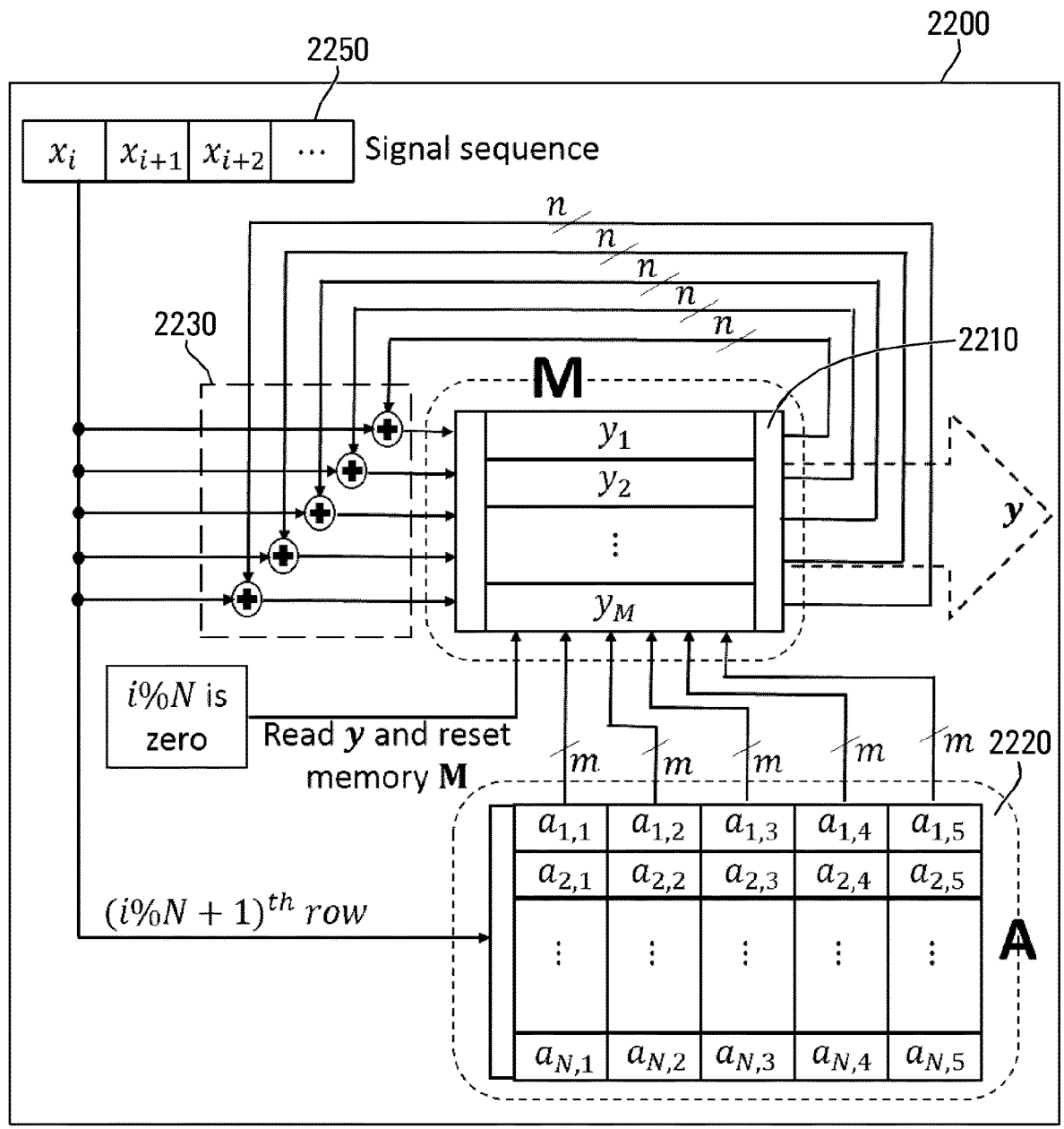
FIG. 22 is a block diagram of an example compressive sensing based compressor.

FIG. 22 is a block diagram of a compressive sensing based compressor 2200, exemplary of an embodiment.

As illustrated, compressive sensing based compressor 2200 comprises a measurement memory 2210 and an address memory 2220. Compressive sensing based compressor 2200 further comprises a bank of 5 adders 2230.

By way of overview, a measurement matrix $\phi$ containing N column vectors $\phi_1, \phi_2, \ldots, \phi_N$ each of which is sparse with unity-valued components placed at randomly selected small number such as, for example, 4 to 6, indices may be employed.

Address memory 2220 may then contain the indices of the columns of 1 containing a total of 5 unity-valued components, with the notation $\{a_{1,1}, a_{1,2}, a_{1,3}, a_{1,4}, a_{1,5}\}$, $\{a_{2,1}, a_{2,2}, a_{2,3}, a_{2,4}, a_{2,5}\}, \ldots, \{a_{N-1,1}, a_{N-1,2}, a_{N-1,3}, a_{N-1,4}, a_{N-1,5}\}$, and $\{a_{N,1}, a_{N,2}, a_{N,3}, a_{N,4}, a_{N,5}\}$ representing the indices for unity-valued components of the column vectors $\phi_1, \phi_2, \ldots, \phi_{N-1}$, and $\phi_N$, respectively.

Compressive sensing based compressor is adapted to compress a signal sequence 2250.

By way of overview, the compressive sensing operation of equation (1) is implemented by FIG. 22, where the measurement vector y is obtained as the vector $y_N$ after running the iteration $$y_i = y_{i-1} + \phi_i x_{i-1} \tag{22}$$

for i=1, 2, ..., N with $y_0=0$, where $\phi_1, \phi_2, \ldots, \phi_N$ are the columns of the measurement matrix $\Phi$.

Figure 23:
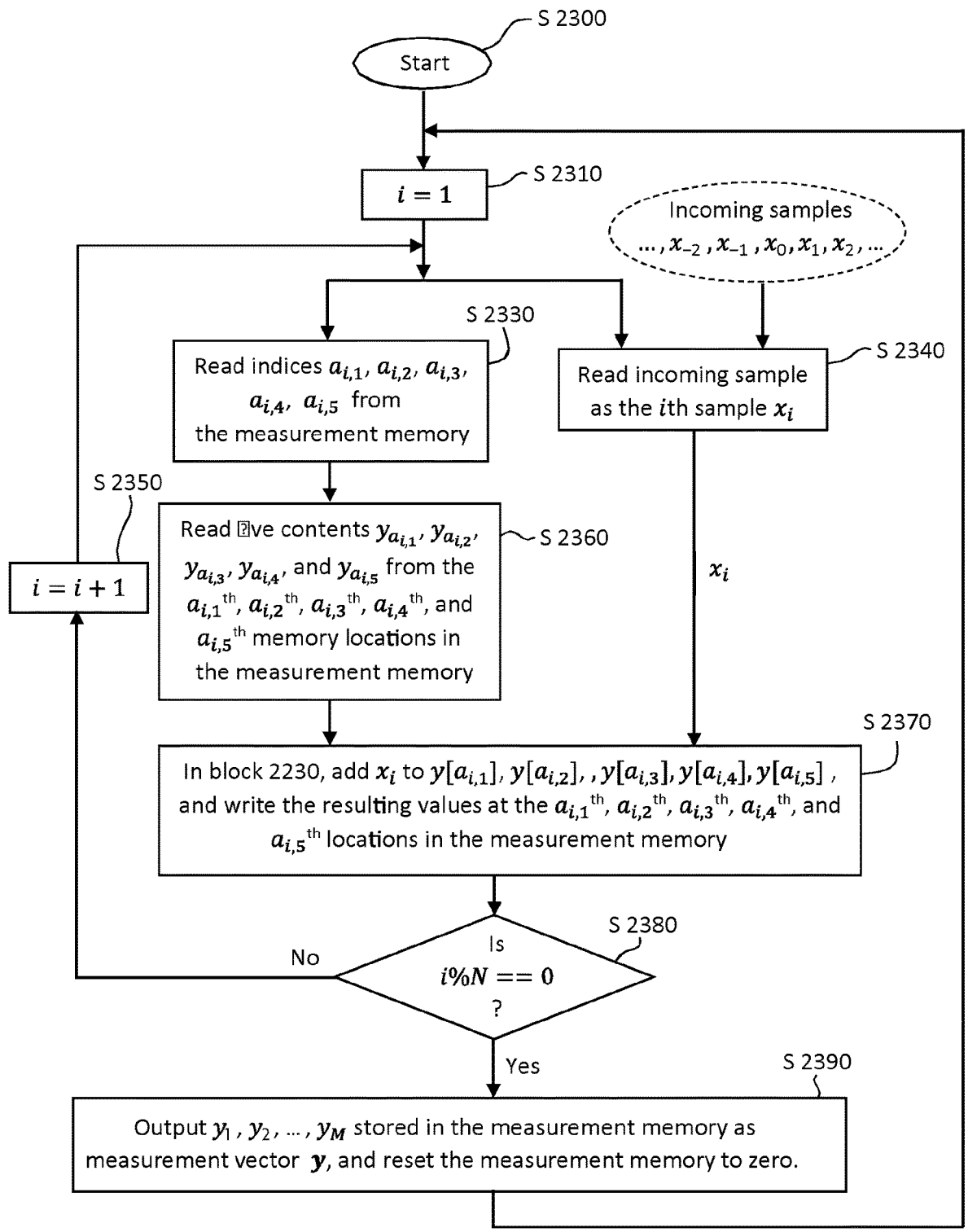
FIG. 23 is a flow diagram showing how a compressive sensing compressor (e.g.

FIG. 23 is an exemplary flow diagram of compressive sensing such as may be performed using compressive sensing based compressor 2200. More particularly, FIG. 23 illustrates the execution of a single, ith, iteration in (22) above.

Operations of compressive sensing based compressor 2200 are described with respect to FIG. 23. In particular, the operation of compressive sensing based compressor is described at blocks S2300 and onwards.

By way of overview, samples $(x_1, x_2, \ldots, x_N, x_{N+1}, x_{N+2}, \ldots x_{2N}, x_{2N+1}, x_{2N+2}, \ldots, x_{3N}, x_{3N+1}, x_{3N+2}), \ldots$ are treated as a sequence of segments, each of length N. Incoming sequences are counted to determine the end of a given segment which may be detected by the count reaching N.

At block S2300, measurement memory 2210 is set to zero, and the operation is started.

Control then passes to block S2310 where the counter i is initialized to 1. Flow control then proceeds in parallel to blocks S2330 and 2340.

At block S2330, values of the indices ai,1, ai,2, ai,3, ai,4, ai,5 are read from the ith row in address memory 2220.

At the same time, at block S2340, for each value of i, a corresponding oncoming sample is read as the ith sample $x_i$.

Once the activities at blocks S2360 and S2340 are both completed, processing proceeds to block S2370.

At block S2370, the contents from the $a_{i,1}$th, $a_{i,2}$th, $a_{i,3}$th, $a_{i,4}$th, and $a_{i,5}$th locations in measurement memory 2210 are read and passed to a corresponding one of adders 2230. The resulting five values are stored back to the $a_{i,1}$th, $a_{i,2}$th, $a_{i,3}$th, $a_{i,4}$th, and $a_{i,5}$th locations in the measurement memory 2210. Processing then proceeds to block S2380.

At block S2380 it is determined whether the end of the given segment has been reached. If i is determined to be smaller than N, control proceeds to block S2350 where index i is incremented and then control returns to blocks S2330 and S2340. Alternatively, if at block S2380 i is determined to be equal to N, then control passes to block S2390. At block S2390, the contents of measurement memory 2210 are read out as the measurement of the signal segment comprising the current and previous N−1 samples and then measurement memory 2210 is reset to zero and control flow returns to block S2310 to begin compressive sensing for the next segment next N signal samples.

Of course, the above described embodiments are intended to be illustrative only and are in no way limiting. Described embodiments are amenable to many modifications of form and arrangement of parts, details and order of operation. The invention is intended to encompass all such modifications within the scope, as defined by the claims.

What is claimed is:

1. A method of detecting QRS complexes in an ECG signal, the method comprising:
   receiving compressively-sensed measurements of the ECG signal;
   constructing an estimate of the ECG signal from the received compressively-sensed measurements;
   computing a first-order difference of the estimate of the ECG signal, wherein constructing the estimate of the ECG signal comprises enforcing a block-sparse structure on the first-order difference of the estimate of the ECG signal; and
   processing the first-order difference of the estimate of the ECG signal to locate one or more significant natural blocks in the block-sparse structure, each indicating a QRS complex in the ECG signal.

2. The method of claim 1, wherein said constructing the estimate of the ECG signal comprises:
   for each block size of a plurality of selected block sizes, generating a reconstructed signal for that block size by applying the $l_{2/p}^d$-RLS algorithm to the compressively-sensed measurements of the ECG signal using said block size and taking the absolute value of each entry in the output of the algorithm;
   computing the estimate of the ECG signal by:
   amplitude scaling each of the reconstructed signals to a selected dynamic range to yield a scaled reconstructed signal for each of the block sizes; and,
   averaging the scaled reconstructed signals.

3. The method of claim 2, wherein applying the $l_{2/p}^d$-RLS algorithm to the compressively-sensed measurements of an ECG signal using a given block size comprises dividing the first-order difference of the ECG signal into blocks of the given block size.

4. The method of claim 2, wherein applying the $l_{2/p}^d$-RLS algorithm to the compressively-sensed measurements of an ECG signal using a given block size comprises dividing the first-order difference of the ECG signal into blocks of cardinality approximately equal to the given block size.

5. The method of claim 2, wherein the boundaries of the blocks are shifted to the right by a block shift time, the block shift time less than the given block size.

6. The method of claim 2, wherein at least two of the reconstructed signals are generated in parallel.

7. The method of claim 1, wherein processing the first-order difference of the estimate of the ECG signal to locate one or more significant natural blocks comprises:

generating a binary signal from the estimate of the ECG signal, the binary signal comprising one or more square pulses defined by adjacent non-zero entries in the signal; and locating the one or more natural blocks based on the locations of the square pulses in the binary signal.

8. The method of claim 7 wherein generating a binary signal from the estimate of the ECG signal, comprises, for each entry in the estimate of the ECG signal, generating a zero-valued entry unless the magnitude of that entry exceeds a threshold.

9. The method of claim 7 wherein the estimate of the ECG signal is smoothed prior to generating the binary signal by applying at least one of a moving average and a low-pass filter to the estimate of the ECG signal.

10. The method of claim 7, wherein locating the one or more natural blocks based on the locations of the square pulses in the binary signal comprises repeatedly applying an erosion-without-termination operator to the binary signal to shrink the square pulses to impulses, each of the impulses corresponding to a location of a natural block.

11. The method of claim 7 further comprising post-processing the binary signal by applying at least one of an erosion operator to fill gaps between adjacent square pulses and a dilation operator to eliminate short square pulses prior to locating the one or more natural blocks.

12. A system for detecting QRS complexes in ECG signals, the system comprising:

a receiver for receiving compressively-sensed measurements of an ECG signal;

a processor coupled to a non-transitory computer-readable storage medium, the medium storing instructions that when executed by the processor cause the processor to perform the method of claim 1.

13. The method of claim 1 wherein a block-sparse structure is enforced on the first-order difference of the estimate of the ECG signal by applying the $l_{2/p}^{d}$-RLS algorithm to the compressively-sensed measurements of the ECG signal.

* * * * *